US010307215B2

(12) United States Patent
Swayze et al.

(10) Patent No.: US 10,307,215 B2
(45) Date of Patent: Jun. 4, 2019

(54) LOCKING ARTICULATING ROBOTIC SURGICAL TOOLS

(71) Applicant: Ethicon LLC, Guaynabo, PR (US)

(72) Inventors: Jeffrey S. Swayze, West Chester, OH (US); Mark Overmyer, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 212 days.

(21) Appl. No.: 15/422,714

(22) Filed: Feb. 2, 2017

(65) Prior Publication Data
US 2018/0214224 A1 Aug. 2, 2018

(51) Int. Cl.
A61B 17/00 (2006.01)
A61B 17/02 (2006.01)
(Continued)

(52) U.S. Cl.
CPC ............ *A61B 34/37* (2016.02); *A61B 17/072* (2013.01); *A61B 17/07207* (2013.01); *A61B 17/295* (2013.01); *A61B 17/320016* (2013.01); *A61B 18/1445* (2013.01); *A61B 17/0218* (2013.01); *A61B 17/062* (2013.01); *A61B 17/3201* (2013.01); *A61B 2017/00221* (2013.01); *A61B 2017/07285* (2013.01); *A61B 2017/2927* (2013.01); *A61B 2017/2946* (2013.01); *A61B 2018/00595* (2013.01); *A61B 2018/00988* (2013.01); *A61B 2018/1455* (2013.01); *A61B 2034/303* (2016.02); *A61B 2090/034* (2016.02)

(58) Field of Classification Search
CPC . A61B 34/37; A61B 17/072; A61B 17/07207; A61B 17/295; A61B 17/320016; A61B 2017/2927; A61B 2017/2946
See application file for complete search history.

(56) References Cited

U.S. PATENT DOCUMENTS 5,716,366 A 2/1998 Yates
2007/0187453 A1 8/2007 Smith et al.
(Continued)

FOREIGN PATENT DOCUMENTS

EP 2772198 A1 9/2014
EP 2889010 A1 7/2015
(Continued)

OTHER PUBLICATIONS

International Search Report and Written Opinion for International App. No. PCT/IB2018/050608 dated May 11, 2018 (12 pages).
(Continued)

Primary Examiner — Katrina M Stransky
(74) Attorney, Agent, or Firm — Mintz Levin/EES

(57) ABSTRACT

Various exemplary systems, devices, and methods are provided for locking articulating surgical tools. In general, a surgical tool can include an elongate shaft having at a distal end thereof an end effector configured to engage tissue. The end effector can be configured to articulate relative to the elongate shaft. The surgical tool can include a locking mechanism configured to lock the end effector at its current angled orientation. The surgical tool can be configured to releasably couple to a robotic surgical system configured to control a variety of movements and actions associated with the surgical tool.

20 Claims, 14 Drawing Sheets

(51) Int. Cl.

| | |
|---|---|
| *A61B 17/29* | (2006.01) |
| *A61B 17/32* | (2006.01) |
| *A61B 34/30* | (2016.01) |
| *A61B 34/37* | (2016.01) |
| *A61B 17/062* | (2006.01) |
| *A61B 17/072* | (2006.01) |
| *A61B 17/295* | (2006.01) |
| *A61B 17/3201* | (2006.01) |
| *A61B 18/14* | (2006.01) |
| *A61B 18/00* | (2006.01) |
| *A61B 90/00* | (2016.01) |

(56) References Cited

U.S. PATENT DOCUMENTS

| | | | |
|---|---|---|---|
| 2010/0264193 A1 | 10/2010 | Huang et al. | |
| 2013/0334278 A1* | 12/2013 | Kerr | A61B 17/07207 227/175.1 |
| 2014/0239041 A1* | 8/2014 | Zerkle | A61B 17/07207 227/176.1 |
| 2014/0276776 A1 | 9/2014 | Parihar et al. | |

FOREIGN PATENT DOCUMENTS

| | | |
|---|---|---|
| WO | WO-2014151621 A1 | 9/2014 |
| WO | WO-2014151952 A1 | 9/2014 |

OTHER PUBLICATIONS

U.S. Appl. No. 15/200,283 entitled "Methods, Systems, and Devices for Initializing a Surgical Tool" filed Jul. 1, 2016.

U.S. Appl. No. 15/237,648 entitled "Methods, Systems, and Devices for Causing End Effector Motion With a Robotic Surgical System" filed Aug. 16, 2016.

U.S. Appl. No. 15/237,653 entitled "Methods, Systems, and Devices for Controlling a Motor of a Robotic Surgical Systems" filed Aug. 16, 2016.

U.S. Appl. No. 15/385,935 entitled "Laterally Actuatable Articulation Lock Arrangements for Locking an End Effector of a Surgical Instrument in an Articulated Configuration" filed Dec. 21, 2016.

* cited by examiner

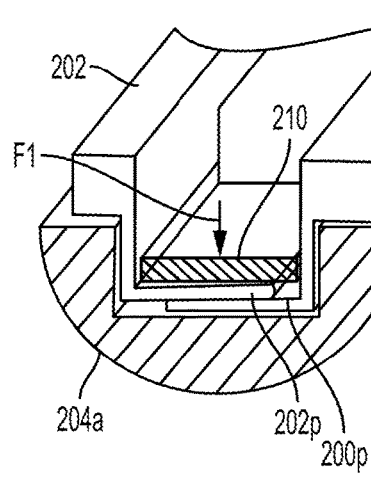
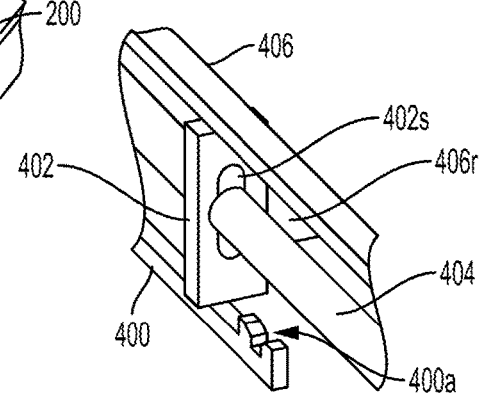
FIG. 15  FIG. 16
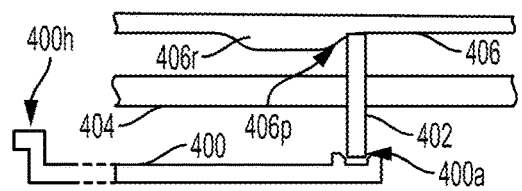
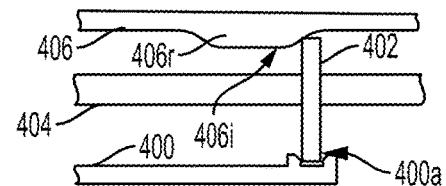
FIG. 17  FIG. 18
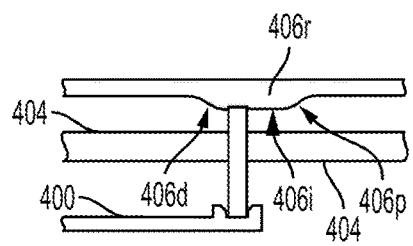
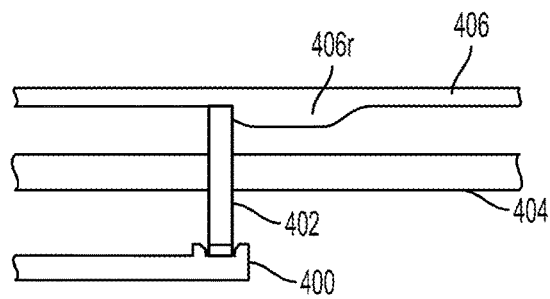
FIG. 19  FIG. 20

LOCKING ARTICULATING ROBOTIC SURGICAL TOOLS

FIELD

Methods and devices are provided for robotic surgery, and in particular for locking articulating robotic surgical tools.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, systems, devices, and methods for locking articulating robotic surgical tools are provided.

In one aspect, a surgical device is provided that in one embodiment includes an elongate shaft, and an end effector at a distal end of the elongate shaft. The end effector is configured to articulate at an angle relative to a longitudinal axis of the elongate shaft. The surgical device also includes a cutting element configured to move longitudinally along the end effector to cut tissue engaged by the end effector, and a locking mechanism configured to lock the end effector at the angle in response to the movement of the cutting element along the end effector.

The surgical device can vary in any number of ways. For example, the rod can include first and second rods configured to move longitudinally relative to the end effector to thereby cause the end effector to articulate, and each of the first and second rods can be configured to be operatively engaged by the locking mechanism to lock the end effector. For another example, the locking mechanism can be configured to lock the end effector at any angle in the end effector's range of articulation. For yet another example, the locking mechanism can include a pair of plates configured to frictionally engage with one another to lock the end effector at the angle until a force is applied thereto to overcome the frictional engagement. For another example, the locking mechanism can include a gear having teeth configured to operatively engage corresponding teeth of a rod configured to move the cutting element, and the gear can be configured to rotate during the movement of the cutting element along the end effector. For yet another example, the locking mechanism can include a plate configured to operatively engage a rod configured to move the cutting element, and the plate can be configured to move longitudinally with the cutting element during the movement of the cutting element along the end effector. For still another example, the movement of the cutting element can be configured to be controlled by a robotic surgical system.

In another embodiment, a surgical device is provided that includes an elongate shaft, and an end effector at a distal end of the elongate shaft. The end effector is configured to articulate at an angle relative to a longitudinal axis of the elongate shaft. The surgical device also includes a rod configured to move longitudinally relative to the end effector to thereby cause the end effector to articulate, a cutting element configured to move longitudinally along the end effector to cut tissue engaged by the end effector, and a locking mechanism configured to automatically move relative to the end effector in response to the movement of the cutting element to thereby hold the end effector at the angle.

The device can have any number of variations. For example, the locking mechanism can be configured to move during the articulation of the end effector. For another example, the locking mechanism can be configured to move during the movement of the cutting element. For yet another example, the movement of the locking mechanism can include longitudinal movement. For still another example, the movement of the locking mechanism can include rotational movement. For another example, the surgical device can include an actuator configured to be actuated to cause the movement of the cutting element, and the locking mechanism can be configured to move relative to the end effector in response to the actuation of the actuator. For yet another example, the surgical device can include an actuator configured to be actuated to cause the articulation of the end effector, and the locking mechanism can be configured to move relative to the end effector in response to the actuation of the actuator. For another example, the locking mechanism can include a pair of surfaces configured to frictionally engage to hold the end effector at the angle until a force is applied thereto to overcome the frictional engagement. For yet another example, the locking mechanism can include a gear having teeth configured to operatively engage corresponding teeth of the rod and to rotate during the movement of the cutting element along the end effector. For still another example, the locking mechanism can include a plate configured to operatively engage the rod and to move longitudinally with the cutting element during the movement of the cutting element along the end effector. For yet another example, the movement of the cutting element and the movement of the rod can be configured to be controlled by a robotic surgical system.

In another aspect, a surgical method is provided that in one embodiment includes actuating a first actuator of a surgical tool having an elongate shaft with an end effector at a distal end thereof, actuation of the first actuator causing the end effector to articulate at any angle up to a maximum angle relative to the elongate shaft. The surgical method also includes actuating a second actuator of the surgical tool to cause a cutting element of the surgical tool to move along the end effector to cut tissue engaged by the end effector. One of actuating the first actuator and actuating the second actuator causes the end effector to be locked at the angle throughout the movement of the cutting element.

The surgical method can vary in any number of ways. For example, actuating the first actuator can cause the end effector to be locked at the angle throughout the movement of the cutting element, and the surgical tool can include a pair of plates configured to engage at a first coefficient of friction in response to the actuation of the first actuator. For another example, actuating the second actuator can cause the end effector to be locked at the angle throughout the movement of the cutting element, actuating the first actuator can cause longitudinal movement of an articulation rod to effect the articulation of the end effector, and the surgical tool can include a movable locking mechanism that moves into engagement with the articulation rod to lock the end effector at the angle throughout the movement of the cutting element. For yet another example, a robotic surgical system operatively coupled to the surgical tool can cause the actuation of the first actuator and can cause the actuation of the second actuator.

BRIEF DESCRIPTION OF THE DRAWINGS

The invention will be more fully understood from the following detailed description taken in conjunction with the accompanying drawings, in which:

FIG. 15 is another perspective, cross-sectional view of a portion of the surgical tool of FIG. 10;

FIG. 16 is a perspective view of a portion of yet another embodiment of a surgical tool;

FIG. 17 is a side view of a portion of the surgical tool of FIG. 16 with a cam of the surgical tool in a first position;

FIG. 18 is a side view of the surgical tool of FIG. 17 with the cam moved from the first position to a second position;

FIG. 19 is a side view of the surgical tool of FIG. 18 with the cam moved from the second position to a third position;

FIG. 20 is a side view of the surgical tool of FIG. 19 with the cam moved from the third position to a fourth position;

DETAILED DESCRIPTION

Figure 1:
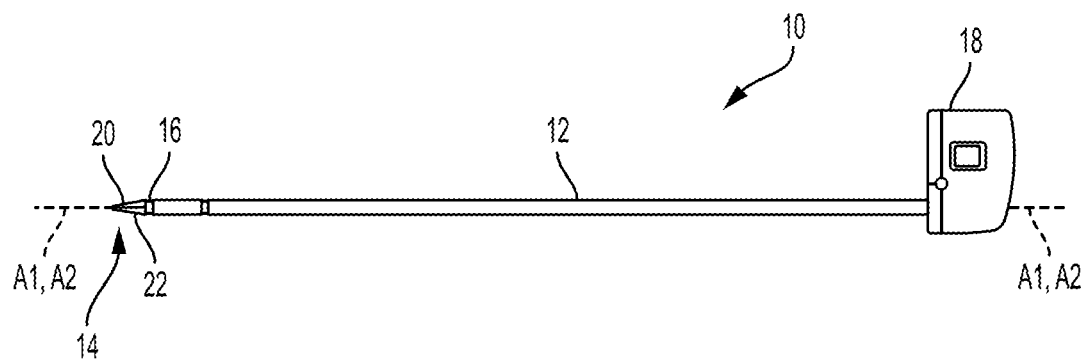
FIG. 1 is a side schematic view of one embodiment of a surgical tool.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary systems, devices, and methods are provided for locking articulating surgical tools. In general, a surgical tool can include an elongate shaft having at a distal end thereof an end effector configured to engage tissue. The end effector can be configured to articulate relative to the elongate shaft, e.g., angularly orient relative to a longitudinal axis of the elongate shaft, which may help the end effector access and securely engage the tissue. The surgical tool can include a cutting element configured to translate longitudinally along the end effector to cut the engaged tissue. When the end effector is articulated, e.g., is angled at a non-zero angle relative to the shaft's longitudinal axis, the longitudinal translation of the cutting element along the end effector exerts a torque force on the end effector that urges the end effector away from its current angled orientation, e.g., urges the end effector toward a substantially zero angle position in which it is substantially aligned with the shaft's longitudinal axis. However, articulating movement of the end effector from its current angled orientation during cutting of the tissue may cause the end effector to undesirably shift in position relative to the engaged tissue such that the tissue is not cut at a proper location, and/or may cause the end effector to undesirably press against matter (e.g., an adjacent body structure, another surgical tool, etc.) in the patient's body that may cause harm to the matter and/or the end effector. The surgical tool can include a locking mechanism configured to lock the end effector at its current angled orientation, which may prevent the end effector from being urged away from its current angled orientation during the translation of the cutting element. The locking mechanism can be configured to lock the end effector at any angle within its possible range of articulation, which may allow a surgeon to position the end effector as desired without being limited to particular articulation angles. In at least some embodiments, the locking mechanism can be configured to lock the articulated position of the end effector before the cutting element begins translating along the end effector, which may help ensure that the cutting element's translation does not cause a change in the articulation angle before the locking mechanism provides the lock. Also, in at least some embodiments, the locking mechanism can be configured to automatically lock the end effector at its current articulation angle in response to a start of the cutting element's translation along the end effector, which may help ensure that the end effector is not prematurely locked in position so its articulation angle can be adjusted prior to a start of the cutting and/or may allow for "foolproof" use of the surgical tool since the locking occurs automatically.

The surgical tool can be configured to releasably couple to a robotic surgical system (also referred to herein as a "surgical robot") configured to control a variety of movements and actions associated with the surgical tool. The robotic surgical system can be configured to control the articulation of the end effector and to control the translation of the cutting element along the end effector. Thus, the robotic surgical system can be configured to control actuation of the locking mechanism, e.g., cause the locking of the end effector. In at least some embodiments, the robotic surgical system can be configured to cause the end effector to be locked at its current angled orientation before the cutting element begins translating along the end effector. Also, in at least some embodiments, the robotic surgical system can be configured to cause the locking mechanism to automatically lock the end effector at its current articulation angle via the robotic surgical system's control input to the surgical tool to start the cutting element's translation along the end effector.

FIG. 1 illustrates one embodiment of a surgical tool 10 that includes an elongate shaft 12, an end effector 14, a wrist 16 that couples the end effector 14 to the shaft 12 at a distal end of the shaft 12, and a tool housing 18 coupled to a proximal end of the shaft 12. The end effector 14 is configured to move relative to the shaft 12 at the wrist 16, e.g., by pivoting at the wrist 16, to position the end effector 14 at a desired location relative to a surgical site during use of the tool 10. The housing 18 includes various components (e.g., gears and/or actuators) configured to control the operation various features associated with the end effector 14 (e.g., any one or more of clamping, firing, rotation, articulation, energy delivery, etc.). In at least some embodiments, the shaft 12, and hence the end effector 14 coupled thereto, is configured to rotate about a longitudinal axis A1 of the shaft 12. In such embodiments, the various components of the housing 18 are configured to control the rotational movement of the shaft 12. In at least some embodiments, as in this illustrated embodiment, the surgical tool 10 is configured to releasably couple to a robotic surgical system, and the tool housing 18 can include coupling features configured to allow the releasable coupling of the tool 10 to the robotic surgical system. Each of the shaft 12, end effector 14, wrist 16, and housing 18 are discussed further below.

The surgical tool 10 can have any of a variety of configurations. In general, the surgical tool can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 10 in at least some embodiments is configured to apply energy (such as radiofrequency (RF) energy) to tissue, while in other embodiments the tool 10 is not configured to apply energy to tissue.

The shaft 12 can have any of a variety of configurations. In general, the shaft 12 is an elongate member extending distally from the housing 18 and having at least one inner lumen extending therethrough. The shaft 12 is fixed to the housing 18, but in other embodiment the shaft 12 can be releasably coupled to the housing 18 such that the shaft 12 can be interchangeable with other shafts. This may allow a single housing 18 to be adaptable to various shafts having different end effectors.

The end effector 14 can have a variety of sizes, shapes, and configurations. The end effector 14 includes a tissue grasper having a pair of opposed jaws 20, 22 configured to move between open and closed positions with one or both of the jaws 20, 22 configured to pivot at the wrist 16 to move the end effector 14 between the open and closed positions. The end effector 14 in other embodiments can have other configurations, e.g., scissors, a babcock, a retractor, etc.

The wrist 16 can have any of a variety of configurations. Exemplary embodiments of a wrist of a surgical tool and of effecting articulation at the wrist are described in International Pat. Pub. No. WO 2014/151952 entitled "Compact Robotic Wrist" filed on Mar. 13, 2014, International Pat. Pub. No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and U.S. patent application Ser. No. 15/237,648 entitled "Methods, Systems, And Devices For Causing End Effector Motion With A Robotic Surgical System" filed on Aug. 16, 2016, which are hereby incorporated by reference in their entireties. In general, the wrist 16 can include a joint configured to allow movement of the end effector 14 relative to the shaft 12, such as a pivot joint at which the jaws 20, 22 are pivotally attached. In some embodiments, the pivoting motion can include pitch movement about a first axis of the wrist 16 (e.g., a X axis), yaw movement about a second axis of the wrist 16 (e.g., a Y axis), and combinations thereof to allow for 360° rotational movement of the end effector 14 about the wrist 16. In other embodiments, the pivoting motion can be limited to movement in a single plane, e.g., only pitch movement about the first axis of the wrist 16 or only yaw movement about the second axis of the wrist 16, such that end effector 14 rotates in a single plane.

Figure 2:
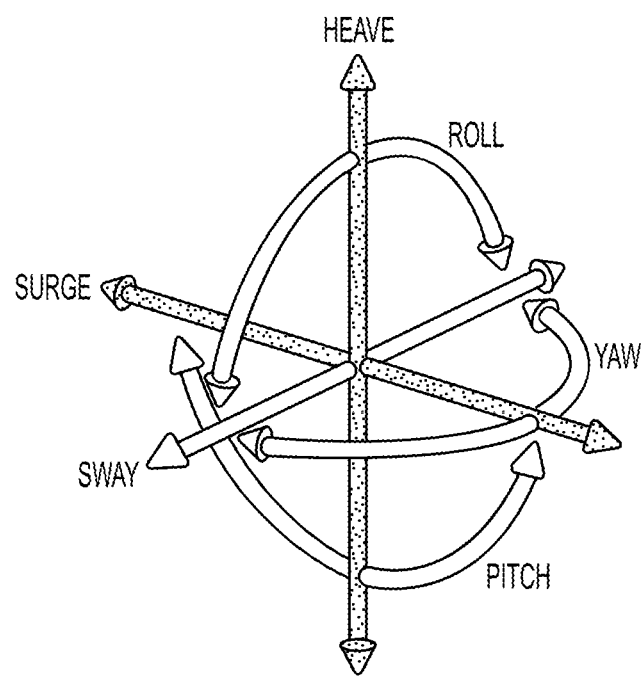
FIG. 2 is a graphical representation of terminology associated with six degrees of freedom.

FIG. 2 illustrates degrees of freedom of a system represented by three translational or position variables, e.g., surge, heave, sway, and by three rotational or orientation variables, e.g., Euler angles or roll, pitch, yaw, that describe the position and orientation of a component of a surgical system with respect to a given reference Cartesian frame. As used herein, and as illustrated in FIG. 2, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right.

The movement of the end effector 14 in this illustrated embodiment includes articulating movement of the end effector 14 between an unarticulated position, in which the end effector 14 is substantially longitudinally aligned with the shaft 12 (e.g., a longitudinal axis A2 of the end effector 14 is substantially aligned with the longitudinal axis A1 of the shaft 12 such that the end effector 14 is at a substantially zero angle relative to the shaft 12), and an articulated position, in which the end effector 14 is angularly orientated relative to the shaft 12 (e.g., the longitudinal axis A2 of the end effector 14 is angled relative to the longitudinal axis A1 of the shaft 12 such that the end effector 14 is at a non-zero angle relative to the shaft 12). A person skilled in the art will appreciate that the end effector 14 may not be precisely aligned with the shaft 12 (e.g., may not be at a precise zero angle relative thereto) but nevertheless be considered to be aligned with the shaft 12 (e.g., be at a substantially zero angle) due to any number of factors, such as manufacturing tolerance and precision of measurement devices. The end effector 14 is shown in the unarticulated position in FIG. 1. The movement of the end effector 14 in this illustrated embodiment also includes rotational movement of the end effector 14 in which the end effector 14 rotates about its longitudinal axis A2, either with or without corresponding rotation of the shaft 12 about its longitudinal axis A1.

The surgical tool 10 can include one or more actuation shafts configured to facilitate movement of the end effector 14. Each of the one or more actuation shafts can extend along the shaft 12 (e.g., in an inner lumen thereof) and can be operatively coupled to the housing 18 and to the end effector 14. In this way, a tool driver coupled to the housing 18 can be configured to provide input to the surgical tool 10 via the tool housing 18 and thereby actuate the one or more actuation shafts to cause movement of the end effector 14.

Figure 3:
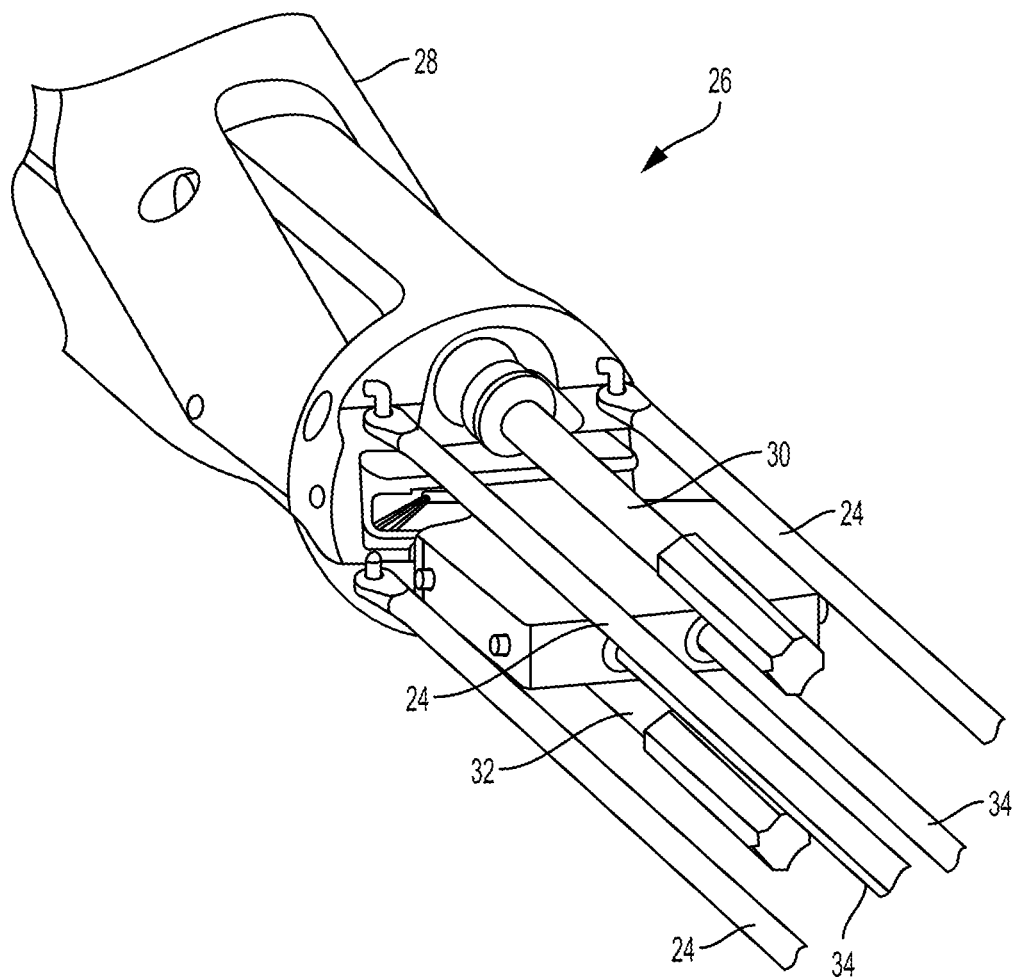
FIG. 3 is a perspective view of a wrist portion of another embodiment of a surgical tool.

FIG. 3 illustrates one embodiment of a surgical tool, such as the tool 10 of FIG. 1, that includes one or more actuation shafts 24 configured to be actuated to cause movement of an end effector 36 (see FIG. 4) operatively coupled thereto. FIG. 3 illustrates a distal end of the actuation shafts 24 extending from a wrist 26 located just proximal of the end effector 36. The wrist 26 can allow for fine movements and angulation of the end effector 36 relative to the proximal end of an elongate shaft 28 to which the end effector 36 is coupled. In this illustrated embodiment, the wrist 26 includes three actuation shafts 24, each in the form of a rod, that are spaced around a perimeter of the wrist 26. When actuated, pushed, pulled, rotated), the actuation shafts 24 will cause articulation of the end effector (e.g., movement up, down, left, right, and combinations thereof) relative to the shaft 28. The actuation shafts 24 are configured to be operatively coupled to a tool driver, via a tool housing of the surgical tool as discussed herein, to cause selective proximal and distal movement of selected one or more of the actuation shafts 24 to cause selected articulation of the end effector 36.

The wrist 26 also includes an upper rotary driver 30 that when actuated can cause a pair of jaws of the end effector 36 to close. The upper rotary driver 30 is configured to be operatively coupled to the tool driver, via the tool housing, to cause rotation of the upper rotary driver 30 and hence closure of the end effector 36. The wrist 26 also includes a lower rotary driver 32 that when actuated can cause movement of a sled relative the end effector 36, e.g., can cause the sled to longitudinally translate along the end effector 36. The sled translating along the end effector 36 can cause a cutting element to translate along the end effector 36 to cut tissue engaged by the d effector 36, as discussed further below. The lower rotary driver 32 is configured to be operatively coupled to the tool driver, via the tool housing, to cause rotation of the lower rotary driver 32 and hence translation of the sled along the end effector 36. The wrist 26 can also include at least one linear pull cable 34 that when actuated moves linearly in a proximal direction to cause rapid close of the end effector 36, e.g., rapid closure of the jaws. The at least one linear pull cable 34 is configured to be operatively coupled to the tool driver, via the tool housing, to cause the proximal movement thereof. Exemplary embodiments of the tool driver and operatively coupling the tool driver to actuation members such as the actuation shafts 24, rotary drivers 30, 32, and linear pull cables 34 are further described in U.S. patent application Ser. No. 15/237,648 entitled "Methods, Systems, And Devices For Causing End Effector Motion With A Robotic Surgical System" filed on Aug. 16, 2016, which is hereby incorporated by reference in its entirety.

Figure 4:
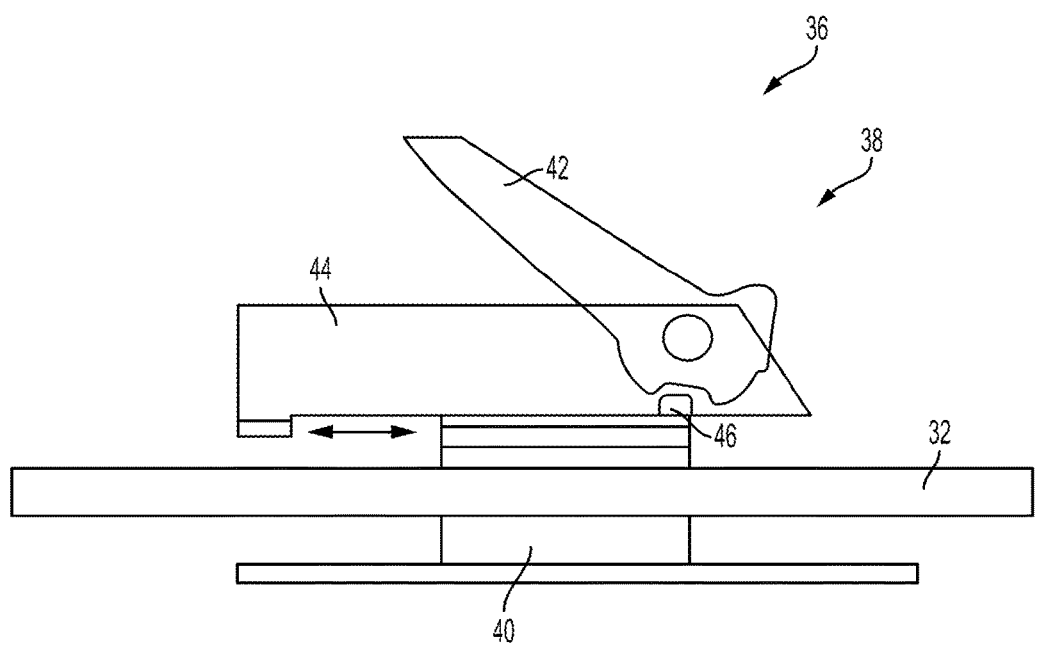
FIG. 4 is a partial side schematic view of one embodiment of an end effector having a knife actuation assembly.

FIG. 4 illustrates a portion of the end effector 36, which has a cutting element actuation assembly 38 that includes a drive member 40, a cutting element 42 in the form of a knife, a sled 44, and the lower rotary driver 32. The drive member 40 includes internal threads that are threadably coupled with the lower rotary driver 32, which is in the form of a lead screw in this illustrated embodiment. Such coupling can allow drive member 40 to move along the lower rotary driver 32 when the lower rotary driver 32 is rotated. As discussed above, the lower rotary driver 32 can be actuated, e.g., via input from a tool driver coupled to the tool's housing, thereby causing rotation of the lower rotary driver 32 and linear movement of the sled 44 along the lower rotary driver 32. The cutting element actuation assembly 38 is configured to orient the cutting element 42 in a cutting position when the drive member 40 pushes the sled 44 distally along the lower rotary driver 32 and to stow the cutting element 42 when the drive member 40 is moved proximally relative to the sled 44. In operation, the lower rotary driver 32 can be rotated to advance the drive member 40 distally along the lower rotary driver 32, thereby pushing the sled 44 in a distal direction and angularly orienting the cutting element 42 in the cutting position. At the end of the distal movement of the assembly 38, the direction of rotation of the lower rotary driver 32 is reversed to retract the drive member 40 proximally relative to the sled 44, thereby causing the cutting element 42 to rotate down into the stowed position, such as via interaction between an interface feature 46 and the cutting element 42.

Figure 5:
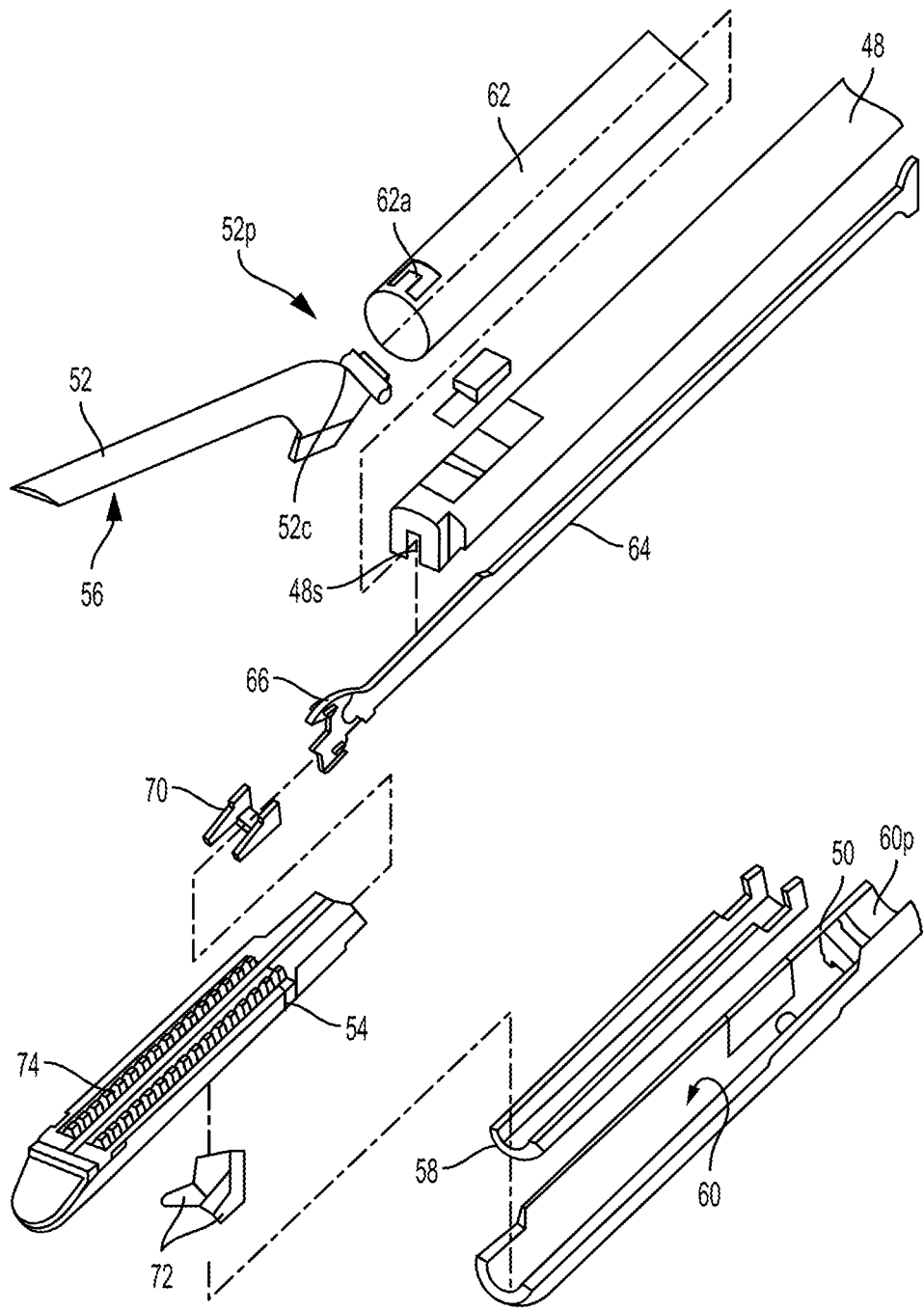
FIG. 5 is an exploded view of a distal portion of another embodiment of a surgical tool.

In at least some embodiments, the surgical tool 10 of FIG. 1 can be a stapler, as mentioned above. FIG. 5 illustrates a distal portion of one embodiment of a surgical stapling tool. The stapler includes an elongate shaft 48 and an end effector at a distal end of the shaft 48. A tool housing (not shown) is at a proximal end of the shaft 48, as discussed herein. The end effector in this illustrated embodiment includes opposed lower and upper jaws 50,52. The lower jaw 50 includes a staple channel configured to support a staple cartridge 54, and the upper jaw 52 has an anvil surface 56 that faces the lower jaw 50 and is configured to operate as an anvil to help deploy staples of the staple cartridge 54 (the staples are obscured in FIG. 5). At least one of the lower and upper jaws 50, 52 is moveable relative to the other of the lower and upper jaws 50, 52 to clamp tissue and/or other objects disposed therebetween. In at least some embodiments, one of the lower and upper jaws 50, 52 can be fixed or otherwise immovable. In some other embodiments, both of the lower and upper jaws 50, 52 be movable. Components of a firing system can be configured to pass through at least a portion of the end effector to eject the staples into the clamped tissue. A cutting element 59 (see FIG. 6), which is a knife blade in this illustrated embodiment, can be associated with the firing system to cut tissue during a stapling procedure.

In this illustrated embodiment, the lower jaw 50 serves as a cartridge assembly or carrier, and the upper jaw 52 serves as an anvil. The staple cartridge 54, having a plurality of staples therein, is supported in a staple tray 58, which in turn is supported within a cartridge channel 60 of the lower jaw 50. The upper jaw 52 has a plurality of staple forming pockets (not shown), each of which is positioned above a corresponding staple from the plurality of staples contained within the staple cartridge 54. The upper jaw 52 can be connected to the lower jaw 50 in a variety of ways. In the illustrated implementation the upper jaw 52 has a proximal pivoting end 52*p* that is pivotally received within a proximal end 60*p* of the staple channel 60, just distal to its engagement to the shaft 48. When the upper jaw 52 is pivoted downwardly, the upper jaw 52 moves the anvil surface 56 and the staple forming pockets formed thereon move toward the opposing staple cartridge 54.

Various clamping components can be used to effect opening and closing of the jaws 50, 52 to selectively clamp tissue therebetween. As illustrated, the pivoting end 52*p* of the upper jaw 52 includes a closure feature 52*c* distal to its pivotal attachment with the cartridge channel 60. Thus, a closure tube 62, whose distal end includes a horseshoe aperture 62*a* that engages the closure feature 52*c*, selectively imparts an opening motion to the upper jaw 52 during proximal longitudinal motion and a closing motion to the upper jaw 52 during distal longitudinal motion of the closure tube 62 in response to input from the tool driver operatively coupled thereto. As mentioned above, the opening and closure of the end effector may be effected by relative motion of the lower jaw 50 with respect to the upper jaw 52, relative motion of the upper jaw 52 with respect to the lower jaw 50, or by motion of both jaws 50, 52 with respect to one another.

Figure 6:
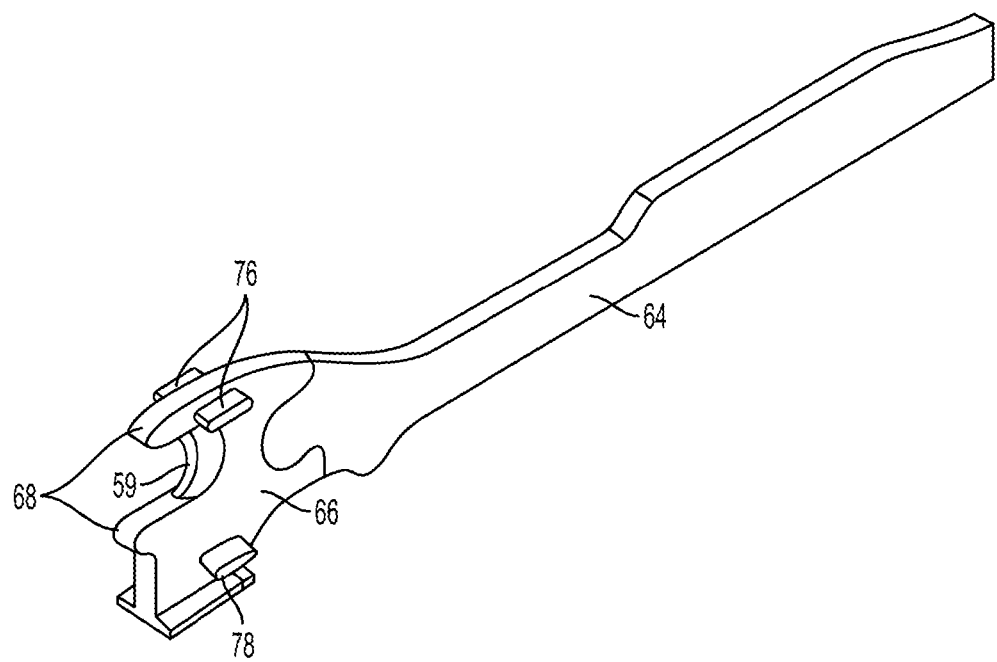
FIG. 6 is a perspective view of a firing bar of the surgical tool of FIG. 5, the firing bar having an E-beam at a distal end thereof.

The firing components of the illustrated embodiment includes a firing bar 64, shown in FIGS. 5 and 6, which has an E-beam 66 on a distal end thereof. The firing bar 64 is flexible in at least a distal portion thereof to facilitate bending of the firing bar 64 at the joint where the end effector is articulated. The firing bar 64 is disposed within the shaft 48, for example in a longitudinal firing bar slot 48*s* of the shaft 48, and guided by a firing input received by the stapler from a tool driver coupled thereto. The firing input can cause distal motion of the E-beam 66 through at least a portion of the end effector to thereby cause the firing of staples contained within the staple cartridge 54. As in this illustrated embodiment, guides 68 projecting from a distal end of the E-Beam 66 can engage a sled 70, which in turn can push staple drivers 72 upwardly through staple cavities 74 formed in the staple cartridge 54. Upward movement of the staple drivers 72 applies an upward force on each of the plurality of staples within the cartridge 54 to thereby push the staples upwardly against the anvil surface 56 of the upper jaw 52 and create formed staples.

In addition to causing the firing of staples, the E-beam 66 can be configured to facilitate closure of the jaws 50, 52, spacing of the upper jaw 52 from the staple cartridge 54, and/or cutting of tissue captured between the jaws 50, 52. In particular, a pair of top pins 76 and a pair of bottom pins 78 (one of the bottom pins 78 is obscured in FIG. 6) can engage one or both of the upper and lower jaws 50, 52 to compress the jaws 50, 52 toward one another as the firing bar 64 advances distally through the end effector. Simultaneously, the cutting element 59 can be configured to cut tissue captured between the jaws 50, 52.

The systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the robotic surgical system can be wired, all electronic communication in the robotic surgical system can be wireless, or some portions of the robotic surgical system can be in wired communication and other portions of the system can be in wireless communication.

Figure 7:
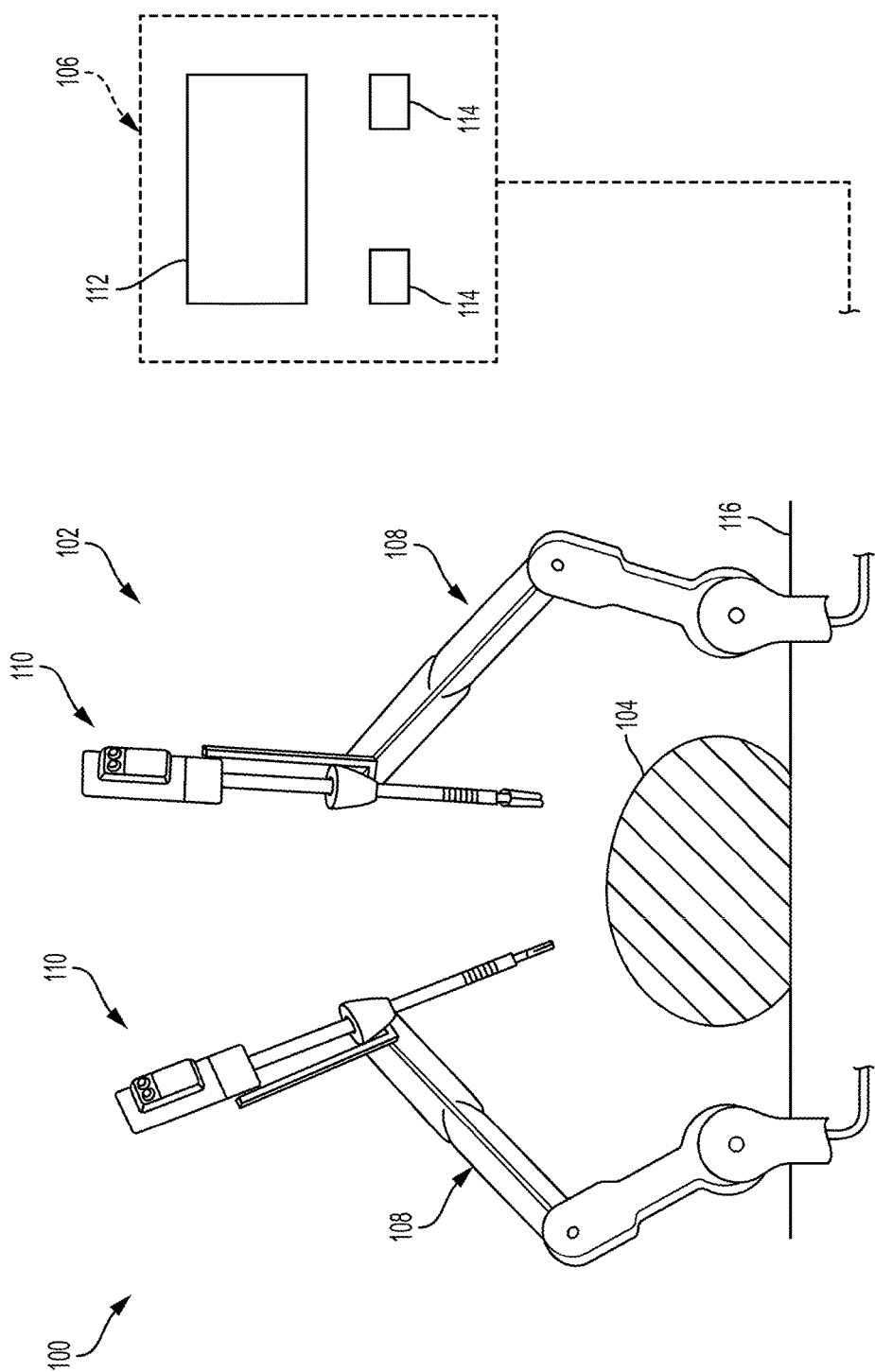
FIG. 7 is a perspective view of one embodiment of a robotic surgical system that includes a patient-side portion and a user-side portion.

FIG. 7 is a perspective view of one embodiment of a robotic surgical system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each tool assembly 110 during a surgical procedure.

The control system 114 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and tool assemblies 110.

The patient-side portion 102 can have a variety of configurations. As illustrated in FIG. 7, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 7). Alternatively, the patient-side portion 102 can include a single assembly that includes one or more robotic arms 108 extending therefrom.

Figure 8:
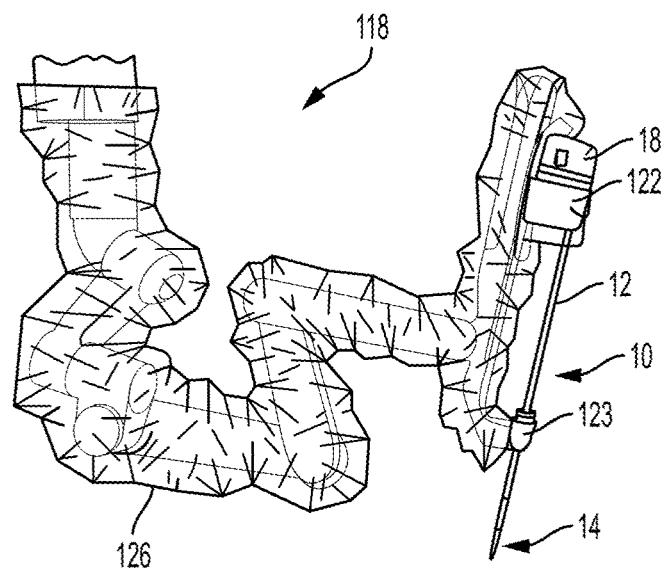
FIG. 8 is a perspective view of one embodiment of a robotic arm of a robotic surgical system with the surgical tool of FIG. 1 releasably and replaceably coupled to the robotic arm.

FIG. 8 illustrates another embodiment of a robotic arm 118 and the surgical tool 10 of FIG. 1 releasably and replaceably coupled to the robotic arm 118. Other surgical instruments can instead be coupled to the arm 118, as discussed herein. The robotic arm 118 is configured to support and move the associated tool 10 along one or more degrees of freedom (e.g., all six Cartesian degrees of freedom, five or fewer Cartesian degrees of freedom, etc.).

The robotic arm 118 can include a tool driver 122 at a distal end of the robotic arm 118, which can assist with controlling features associated with the tool 10. The robotic arm 118 can also include an entry guide 123 (e.g., a cannula mount, cannula, etc.) that can be a part of or releasably and replaceably coupled to the robotic arm 118, as shown in FIG. 8. A shaft of a tool assembly can be inserted through the entry guide 123 for insertion into a patient, as shown in FIG. 8 in which the shaft 12 of the tool 10 of FIG. 1 is shown inserted through the entry guide 123.

In order to provide a sterile operation area while using the surgical system, a barrier 126 can be placed between the actuating portion of the surgical system (e.g., the robotic arm 118) and the surgical instruments coupled thereto (e.g., the tool 10, etc.). A sterile component, such as an instrument sterile adapter (ISA), can also be placed at the connecting interface between the tool 10 and the robotic arm 118. The placement of an ISA between the tool 10 and the robotic arm 108 can ensure a sterile coupling point for the tool 10 and the robotic arm 118. This permits removal of surgical instruments from the robotic arm 118 to exchange with other surgical instruments during the course of a surgery without compromising the sterile surgical field.

Figure 9:
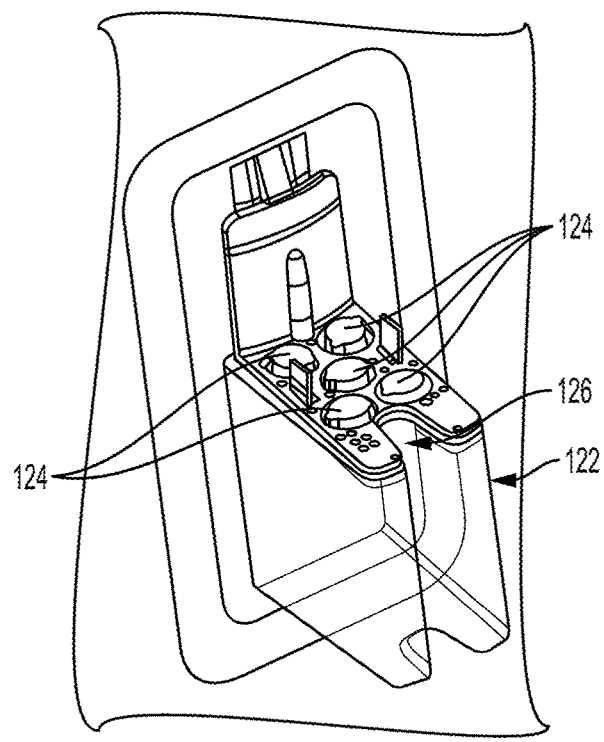
FIG. 9 is a perspective view of a tool driver of the robotic arm of FIG. 8.

FIG. 9 illustrates the tool driver 122 in more detail. As shown, the tool driver 122 includes one or more motors, e.g., five motors 124 are shown, that control a variety of movements and actions associated with the tool 10 coupled to the arm 118. For example, each motor 124 can couple to and/or interact with an activation feature (e.g., gear) associated with the tool 10 for controlling one or more actions and movements that can be performed by the tool 10, such as for assisting with performing a surgical operation. The motors 124 are accessible on the upper surface of the tool driver 122, and thus the tool 10 (e.g., the housing 18 thereof) is configured to mount on top of the tool driver 122 to couple thereto. Exemplary embodiments of motor operation and components of a tool housing (also referred to as a "puck") configured to controlled by tool driver motors are further described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and in U.S. patent application Ser. No. 15/237,653 entitled "Methods, Systems, And Devices For Controlling A Motor Of A Robotic Surgical Systems" filed on Aug. 16, 2016, which is hereby incorporated by reference in its entirety.

The tool driver 122 also includes a shaft-receiving channel 126 formed in a sidewall thereof for receiving the shaft 12 of the tool 10. In other embodiments, the shaft 12 can extend through on opening in the tool driver 122, or the two components can mate in various other configurations.

A surgical tool, such as the tool 10 of FIG. 1, the tool of FIG. 3, the tool of FIG. 5, or other surgical tool, can include a locking mechanism configured to lock an end effector of the surgical tool at any angle of articulation within a range of the end effector's articulation. As also mentioned above, a robotic surgical system, such as the robotic surgical system 100 of FIG. 7 or other robotic surgical system, coupled to the surgical tool can be configured to control actuation of the locking mechanism. Various locking mechanisms for locking an end effector of a surgical instrument in an articulated configuration are described in U.S. patent application Ser. No. 15/385,935 titled "Laterally Actuatable Articulation Lock Arrangements For Locking An End Effector Of A Surgical Instrument In An Articulated Configuration" filed Dec. 21, 2016, which is hereby incorporated by reference in its entirety.

Figure 10:
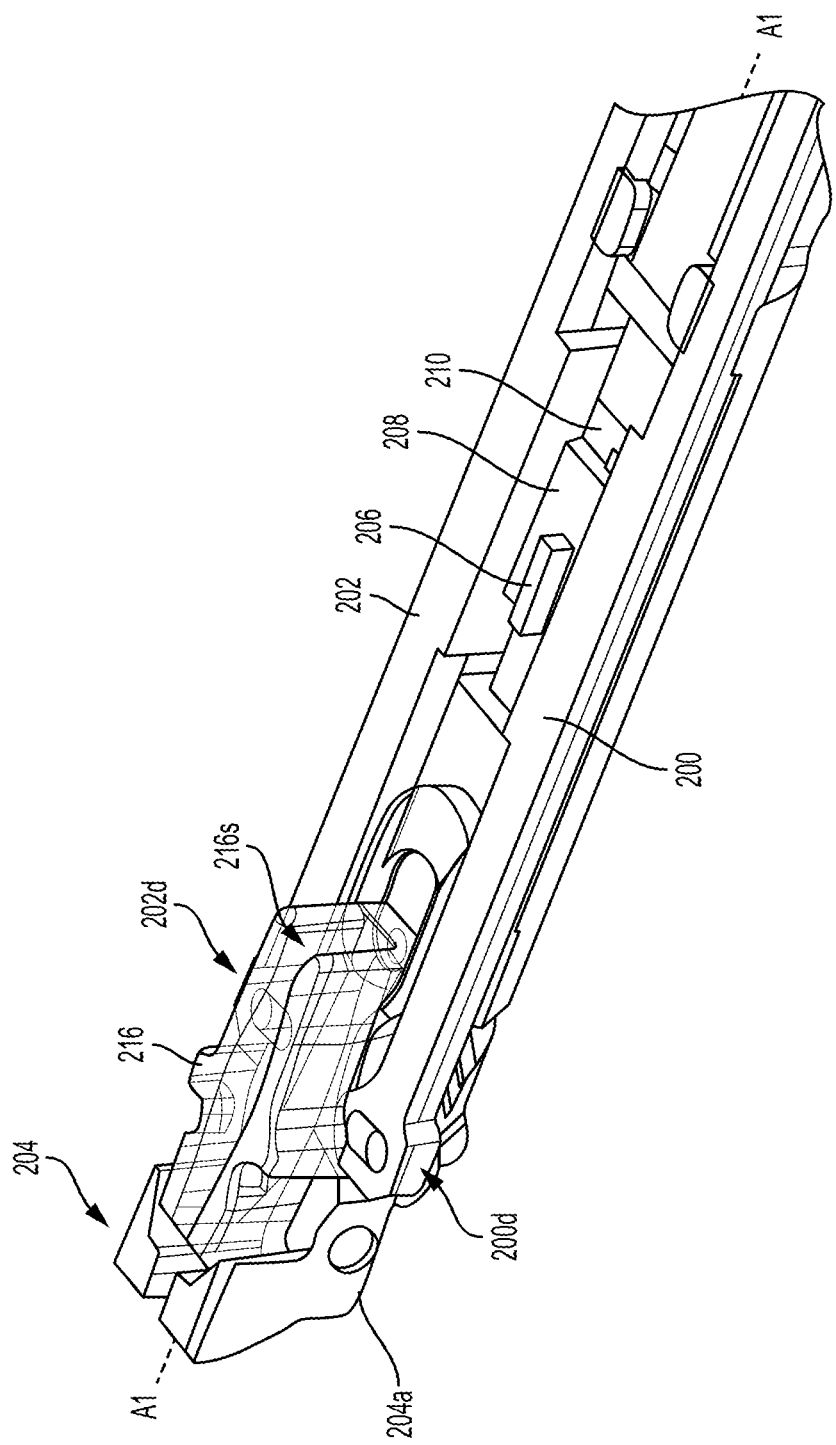
FIG. 10 is a perspective, partially transparent view of a portion of another embodiment of a surgical tool.

FIG. 10 illustrates one embodiment of a surgical tool, such as the tool 10 of FIG. 1, that includes a locking mechanism configured to lock an end effector 204 of the surgical tool any angle of articulation. The surgical tool includes first and second actuation shafts 200, 202, each in the form of a rod, configured to be actuated to cause movement of an end effector 204 operatively coupled thereto. The end effector 204 includes opposed first and second jaws 204a, 204b (see FIG. 14). The first and second actuation shafts 200, 202 are on opposed sides (e.g., left and right) of the surgical tool. The first actuation shaft 200 (on a left side of the tool as illustrated in FIG. 10) has a distal end 200d operatively coupled to the end effector 204, and the second actuation shaft 202 (on a right side of the tool as illustrated in FIG. 10) also has a distal end 202d operatively coupled to the end effector 204. Each of the actuation shaft's distal ends 200d, 202d are coupled to the end effector 204 via respective pegs extending from the end effector 204 that are captured in holes at the distal ends 200d, 202d of the actuation shafts 200, 202, although the coupling can be accomplished in other ways such as by welding, adhesive, etc.

Figure 14:
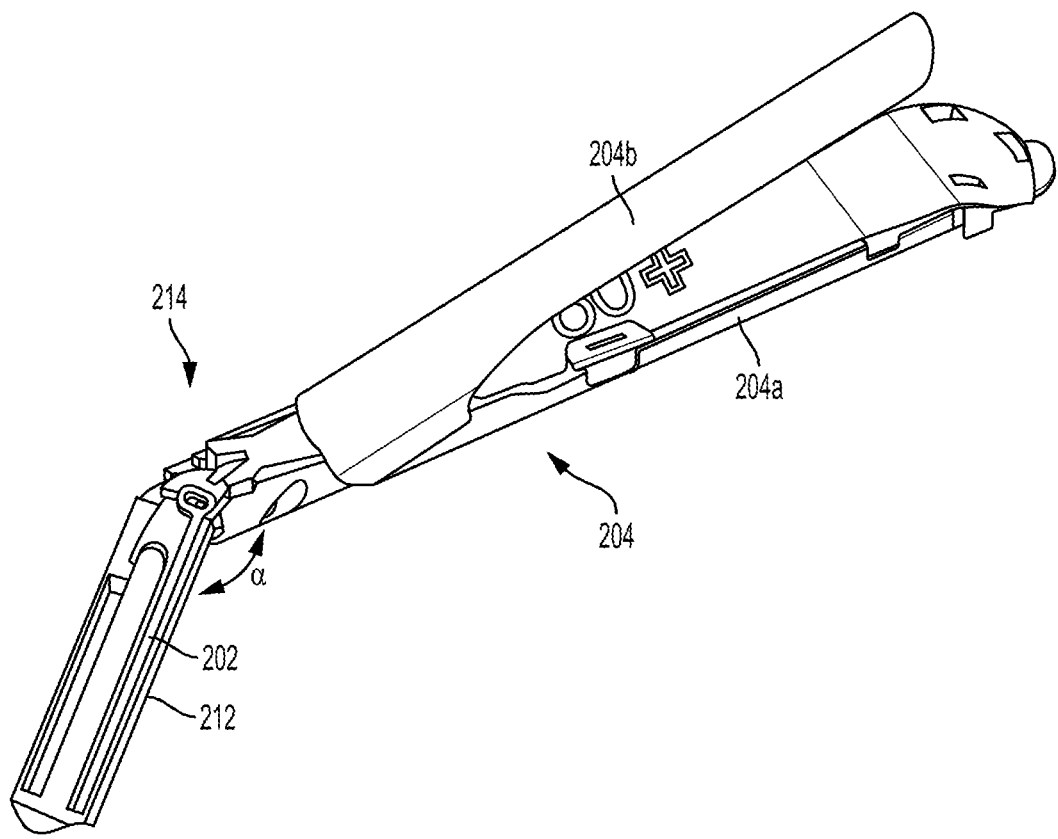
FIG. 14 is a perspective view of a distal portion of the surgical tool of FIG. 10.

The actuation shafts 200, 202 are configured to move relative to each other by longitudinally translating relative to the elongate shaft 212 having the end effector 204 at a distal end thereof at a wrist or joint 214 (see FIG. 14). The actuation shafts 200, 202 extend along the elongate shaft 212, e.g., in an inner lumen thereof. The actuation shafts 200, 202 are configured to simultaneously move in opposite directions, with one of the actuation shafts 200, 202 longitudinally translating in a proximal direction and the other of the actuation shafts 200, 202 longitudinally translating in a distal direction. The end effector 204 is configured to articulate in response to the movement of the first and second actuation shafts 200, 202. A direction of the end effector's angled orientation depends on a direction of the actuation shafts' movement. In response to the first, left-side actuation shaft 200 moving distally and the second, right-side actuation shaft 202 moving proximally, the end effector 204 is configured to angle to the right. In response to the second, right-side actuation shaft 202 moving distally and the first, left-side actuation shaft 200 moving proximally, the end effector 204 is configured to angle to the left. An amount of the actuation shaft's longitudinal movement defines an amount of the articulation, e.g., more longitudinal movement corresponds to a higher angle of articulation. The actuation shafts 200, 202 are configured to be operatively coupled to a tool driver, via a tool housing of the surgical tool as discussed herein, to cause selective proximal and distal movement of the actuation shafts 200, 202 to cause selected articulation of the end effector 204.

Figure 11:
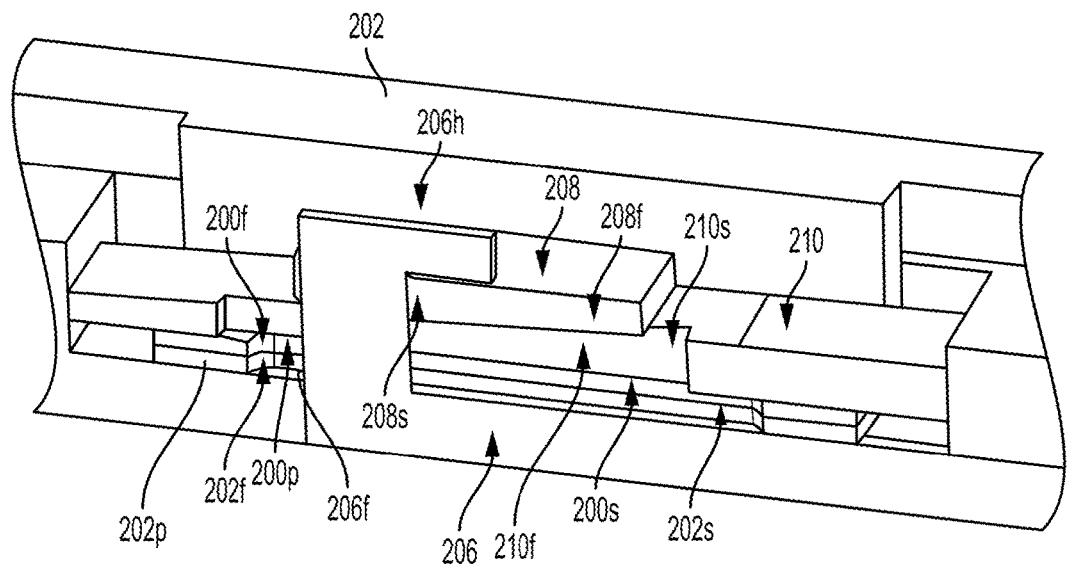
FIG. 11 is a perspective, cross-sectional view of a portion of the surgical tool of FIG. 10.
Figure 12:
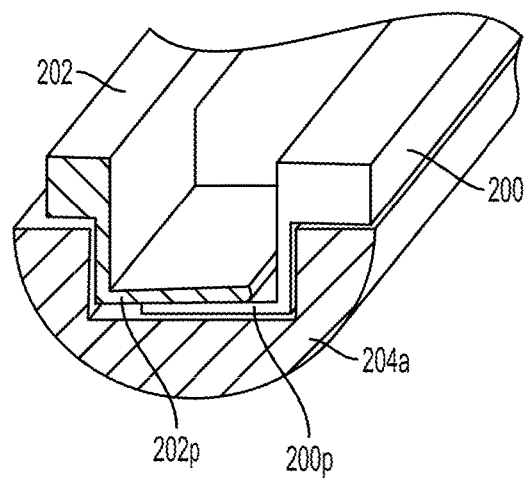
FIG. 12 is another perspective, cross-sectional view of a portion of the surgical tool of FIG. 10.

As shown in FIGS. 11 and 12, each of the actuation shafts 200, 202 includes a plate 200p, 202p that overlap one another. The first plate 200p is above the second plate 202p such that a bottom surface of the first plate 200p faces a top surface of the second plate 202p in this illustrated embodiment, but the second plate 202p can be above the first plate 200p such that a bottom surface of the second plate 202p faces a top surface of the first plate 200p. The first and second plates 200p, 202p are integrally formed with their respective actuation shafts 200, 202 in this illustrated embodiment, which may facilitate manufacturing. In other embodiments the actuation shafts 200, 202 can be separate components from a remainder of their respective actuation shafts 200, 202 and attached thereto using, e.g., welding, adhesive, etc. The actuation shafts 200, 202 are configured to slidably engage one another at the first and second plates 200p, 202p, as discussed further below. Each of the actuation shafts 200, 202 has an elongate slot 200s, 202s formed therein, e.g., formed in the first and second plates 200p, 202p, as shown in FIG. 11. The elongate slots 200s, 202s extend longitudinally, e.g., proximal-distal.

The surgical tool's locking mechanism is configured to move between a locked configuration, in which the end effector 204 is locked at its current articulated angle, and an unlocked configuration, in which the end effector 204 is configured to be freely articulated. The unlocked configuration of the locking mechanism corresponds to the end effector 204 being at a substantially zero angle position. The locking mechanism is operatively coupled to the first and second actuation shafts 200, 202. The locking mechanism is configured to lock the actuation shafts 200, 202 in position relative to one another and to the elongate shaft 212 along which the actuation shafts 200, 202 extend. In other words, the locking mechanism is configured to prevent the actuation shafts 200, 202 from translating longitudinally such that the end effector 204 is held at its current angled orientation.

Figure 13:
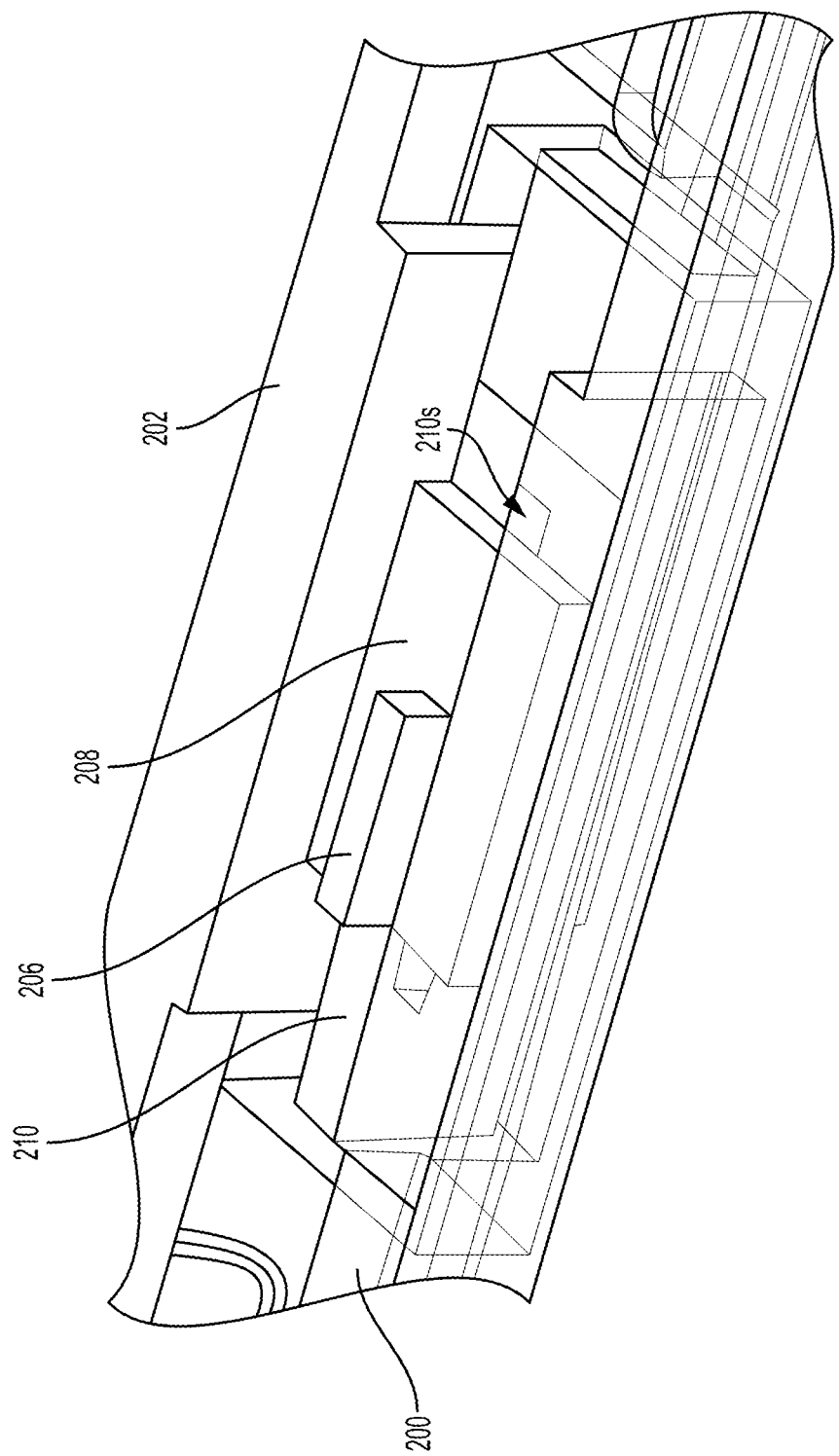
FIG. 13 is a perspective, partially transparent view of a portion of the surgical tool of FIG. 10.

As shown in FIGS. 10, 11, and 13, the locking mechanism in this illustrated embodiment includes a locking rod 206, a movable wedge 208, and a stationary wedge 210. Each of the movable wedge 208 and the stationary wedge 210 has an elongate slot 208s, 210s formed therein, as shown in FIGS. 11 and 13. The elongate slots 208s, 210s extend longitudinally and are aligned along at least partial longitudinal lengths thereof with the elongate slots 200s, 202s of the first and second plates 200p, 202p so as to form a continuous opening through the first and second plates 200p, 202 and the wedges 208, 210. The locking rod 206 extends through the four elongate slots 200s, 202s, 208s, 210s, e.g., extends through the defined opening, in a direction that is substantially perpendicular to a longitudinal axis A1 of the tool, e.g., substantially perpendicular to a direction of the actuation shafts' longitudinal movement. The locking rod 206 has a hook 206h at its distal end that extends through the elongate slots 200s, 202s, 208s, 210s and faces proximally. The hook 206h hooks the movable wedge 208 and is configured to cause movement of the movable wedge 208 relative to the stationary wedge 210, as discussed further below.

The movable wedge 208 and the stationary wedge 210 having facing engaged surfaces 208f, 210f, as shown in FIG. 11. The facing engaged surfaces 208f, 210 taper in opposite directions. The surface 208f of the movable wedge 208 tapers downwardly, e.g., distally, and the surface 210f of the stationary wedge 210 tapers upwardly, e.g., proximally.

The locking mechanism is located near and just proximal of the end effector 204, the joint 214, and the distal ends 200d, 202d of the actuation shafts 200, 202. The locking mechanism is located near a distal end of the elongate shaft 212. The locking mechanism being located near the end effector 204, the joint 214, and the distal ends 200d, 202d of the actuation shafts 200, 202 may help the locking mechanism securely lock the end effector 204 at its current articulated orientation.

The surgical tool also includes a cutting element configured to translate along the end effector 204 to cut tissue engaged thereby, e.g., cut tissue clamped between the jaws 204a, 204b. The surgical tool includes a guide 216 configured to guide the cutting element longitudinally through an elongate slot 216s thereof. For example, the surgical tool can include a firing bar, similar to the firing bar 64 of FIGS. 5 and 6 that includes a cutting element 59, configured to longitudinally translate through the guide 216.

In use, the actuation shafts 200, 202 are actuated, e.g., via force delivered to the surgical tool via a robotic surgical system, to articulate the end effector 204 at an angle relative to the elongate shaft 212. FIG. 14 illustrates one example of an articulated position of the end effector 204, with the end effector 204 at an angle α relative to the elongate shaft 212. For clarity of illustration, the second actuation shaft 202 is shown in FIG. 14 but the first actuation shaft 200, cutting element, guide 216, and locking mechanism are not shown in FIG. 14. The end effector 204 is angled to the right in this illustrated embodiment, caused by the first actuation shaft 200 moving in a distal direction and the second actuation shaft 202 moving in a proximal direction.

As one of the actuation shafts 200, 202 translates proximally, the second actuation shaft 202 in this illustrated embodiment, a proximal-facing surface 202f thereof moves to abut against a distal-facing surface 206f of the locking rod 206. In this illustrated embodiment, the surfaces 202f, 206f (or, for articulation in the opposite direction, surfaces 200f, 206f) do not abut one another until the actuation shafts 200, 202 have moved a certain amount before beginning to move the end effector 204 from its substantially zero angle position. In other embodiments, the proximal-facing surfaces 200f, 202f can abut the distal-facing surface 206f when the end effector 204 is in its substantially zero angle position such that any proximal movement of either of the actuations shafts 200, 202 will cause corresponding proximal movement of the locking rod 206.

With the proximal-facing surface 202f of the proximally-moving one of the actuation shafts 202 abutting the distal-facing surface 206f of the locking rod 206, proximal movement of that actuation shaft 202 will push the locking rod 206 proximally. The proximal movement of the locking rod 206 causes corresponding proximal movement of the movable wedge 208, which is hooked thereto. The locking rod 206 will thus pull the movable wedge 208 proximally along the stationary wedge 210, with the locking rod 206 sliding through the elongate slots 200s, 202s, 210s of the actuation shafts 200, 202 and stationary wedge 210. The facing engaged surface 208f of the movable wedge 208 thus slides proximally along the facing engaged surface 210f of the stationary wedge 210. The movement of the movable wedge 208 along the stationary wedge 210 exerts a downward force, shown by arrow F1 in FIG. 15, that causes the plates 200p, 202p of the actuation shafts 200, 202 to press against one another along their facing surfaces. The actuation shafts 200, 202 are thereby locked in position relative to one another such that the end effector 204 is locked in its current articulated orientation, e.g., locked at the angle α, regardless of the value of the angle α within the end effector's range of articulation up to and including its maximum value. The more that the end effector 204 is articulated, e.g., the greater the angle α, the higher the downward force that the movable wedge 208 exerts due to the wedge shapes of the wedges 208, 210, e.g., due to the tapered facing engaged surfaces 208f, 210f. The greater downward force may help hold the end effector 204 at its articulated angle, since the cutting element can exert a greater force to urge the end effector 204 toward its substantially zero angle position the greater the articulation angle α.

The facing planar surfaces of the actuation shafts 200, 202 that are pressed together can each be made from a material such that a coefficient of friction between the surfaces can help hold the surfaces in position relative to one another with a low downward force (F1). In at least some embodiments, the facing surfaces of the actuation shafts 200, 202 that are pressed together can have a friction feature thereon to further help prevent relative movement of the actuation shafts 200, 202. The friction feature can have a variety of configurations, such as coatings on one or both of the facing surfaces configured to frictionally engage one another at a higher coefficient of friction than without the coating(s), a textured surface on one or both of the facing surfaces configured to frictionally engage one another at a higher coefficient of friction than without the textured surface(s), etc.

With the end effector 204 articulated, the cutting element can be translated along the end effector 204, e.g., via force delivered to the surgical tool via a robotic surgical system, to cut tissue engaged by the end effector 204. Because the end effector 204 is locked in its current articulated orientation with the locking mechanism in its locked configuration, the cutting element's translation will not change the articulation angle α. The cutting element can be translated along the end effector 204 to cut tissue engaged by the end effector 204 when the end effector 204 is unarticulated, e.g., is in the substantially zero angle position, in which case the locking mechanism will be in its unlocked configuration.

The locking mechanism can be moved from its locked configuration to its unlocked configuration by the actuation shafts 200, 202 being actuated, e.g., via force delivered to the surgical tool via a robotic surgical system, to move the end effector 204 from its articulated position to its unarticulated position. The locking rod 206 can thus be free to slide distally, and correspondingly move the movable wedge 208 distally, with the locking rod 206 sliding through the elongate slots 200s, 202s, 210s of the actuation shafts 200, 202 and stationary wedge 210. The locking rod 206 can be biased to a distal position, such as with a spring (not shown), to encourage the distal sliding of the locking rod 206.

In other embodiments, a surgical tool can be configured similar to the surgical tool of FIG. 10 but include a different type of locking mechanism configured to cause facing surfaces of first and second actuation shafts configured to abut one another to lock the surgical tool's end effector at its current articulation angle. The locking mechanism in these embodiments can be configured to be automatically moved from its unlocked configuration to its locked configuration in response to actuation of the surgical tool's cutting element, e.g., in response to the cutting element starting its longitudinal translation along the end effector.

FIG. 16 illustrates one embodiment of a surgical tool configured similar to the surgical tool of FIG. 10, e.g., includes a pair of movable actuation shafts, but including a locking mechanism configured to be automatically moved from its unlocked configuration to its locked configuration in response to actuation of the surgical tool's cutting element. In this illustrated embodiment, the locking mechanism includes a stationary wedge, a movable wedge, a locking rod 400, and a cam 402. The locking rod 400 has a hook 400h (see FIG. 17) at its distal end that hooks the movable wedge, similar to the hook 206h discussed above, except that the hook 400h in this illustrated embodiment faces distally instead of proximally. The locking rod 400 in this illustrated embodiment has a groove or channel 400a formed therein at a proximal end thereof. The groove or channel 400a is configured to operatively engage the cam 402 to facilitate locking of the end effector's articulated position, as discussed further below. The groove or channel 400a thus faces the cam plate 402. The cam 402 in this illustrated embodiment is a plate having a rectangular shape but the plate can have another shape, such as an oval, a diamond, a square, etc. The cam 402 has a slot 402s therein configured to allow the cam 402 to move relative to the firing rod 404, as discussed further below.

The surgical tool also includes a firing rod 404 that is configured to be actuated to cause the firing of staples from the surgical tool's end effector and translate a cutting element along the end effector. The firing rod 404 is generally configured and used similar to the firing bar 64 of FIGS. 5 and 6. The cam plate 402 is attached to the firing rod 404 at a fixed position along the longitudinal length of the firing rod 404. The cam 402 is attached to the firing rod 404 via a slot connection in this illustrated embodiment but can be attached thereto in other ways, such as by being adhered thereto with adhesive, welded thereto, molded as a part of the firing rod 404, etc.

The surgical tool also includes a proximal channel retainer 406 that is configured to guide the translational movement of the firing rod 404. The proximal channel retainer 406 extends from a closure tube of the surgical tool, similar to the closure tube 62 discussed above. Exemplary embodiments of proximal channel retainers are further described in U.S. Pat. No. 5,716,366 entitled "Hemostatic Surgical Cutting Or Stapling Instrument" filed Aug. 22, 1996, which is hereby incorporated by reference in its entirety. In this illustrated embodiment, the proximal channel retainer 406 has a ramp 406r thereon that is configured to operatively engage the cam 402. The ramp 406r thus faces the firing rod 404 in this illustrated embodiment, with the cam 402 attached to the firing rod 404 extending upwardly therefrom toward the proximal channel retainer 406 to facilitate engagement of the cam 402 with the ramp 406r. The cam 402 also extends downwardly from the firing rod 404 toward the locking rod 400 to facilitate engagement of the cam 402 with the groove 400a.

In general, the cam 402 is configured to operatively engage the locking rod 400 and the proximal channel retainer 406 during firing, e.g., during the movement of the firing rod 404, to cause the movable wedge to move relative to the stationary wedge, e.g., to slide therealong similar to the movable and stationary wedges 208, 210 discussed above, and thereby press the first and second actuation shafts together, similar to the first and second actuation shafts 200, 202 discussed above. As discussed further below, the cam's engagement with the ramp 406r can causes the cam 402 to be seated in the groove 400a, which can cause the locking rod 400 to move with the firing rod 404 and thereby slide the movable wedge along the stationary wedge to press the first and second actuation shafts together to lock the end effector at its current articulated orientation.

In use, as shown in FIG. 17, the firing rod 404 and the cam 402 are an initial position before firing with the cam 402 being proximal to the ramp 406r and disengaged from the groove 400a. In response to actuation of the firing rod 404, e.g., via force delivered to the surgical tool via a robotic surgical system, the firing rod 404, and thus also the cam 402 attached thereto, moves in a distal direction, as shown in FIG. 18 where the cam 402 and firing rod 404 are each moved distally from their initial position in FIG. 17. The cam 402 engages the ramp 406r and slides along a proximal sloped surface 406p of the ramp 406r, which urges the cam 402 downward such that the cam 402 moves into the groove 400a. The slot 402s in the cam 402 allows this downward movement of the cam 402 relative to the firing rod 404, e.g., allows the cam 402 to move downwardly to seat in the groove 400a.

FIG. 19 illustrates the firing rod's continued distal movement from its position in FIG. 18. The cam 402 has slid down the proximal sloped surface 406p to an intermediate planar surface 406i along which the cam 402 slides. The cam's engagement with the locking rod 400 via the cam's seating the groove 400a causes the locking rod 400 to also move distally. The movable wedge hooked by the locking rod 400 thus also slides distally along the stationary wedge, thereby urging the actuation shafts together to lock the end effector at its articulated position during the firing, e.g., during the firing of staples and the cutting of tissue with the cutting element. A length of the intermediate planar surface 406i can correspond to a longer of a length that the sled translates to drive the staples out of the end effector and a length that the cutting element translates along the end effector to cut tissue engaged thereby. In at least some embodiments, these lengths may be equal. The actuation shafts may thus be pressed together throughout the cutting and firing process such that the end effector's articulation angle is locked throughout the cutting and firing process.

Figure 21:
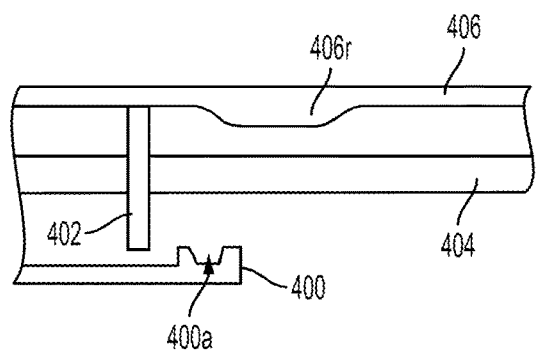
FIG. 21 is a side view of the surgical tool of FIG. 20 with the cam moved from the fourth position to a fifth position.

FIG. 20 illustrates the firing rod's continued distal movement from its position in FIG. 19. The cam 402 has slid along the length of the intermediate planar surface 406i and begins sliding along a distal sloped surface 406d of the ramp 406r. The sliding of the cam 402 along the distal sloped surface 406d allows the cam 402 to move upwardly in a direction away from the locking rod 400 and the groove 400a therein. The surgical tool can include a bias member (not shown), such as a spring in the slot 402s, that biases the cam 402 upwardly toward the proximal channel retainer 406 so the cam 402 automatically moves upwardly out of the groove 400a when the cam 402 encounters the distal sloped surface 406d. The upward bias of the cam 402 may also help the cam 402 smoothly slide along the ramp 406r. Continued distal movement of the firing rod 404 disengages the cam 402 from the groove 400a and from the ramp 406r, as shown in FIGS. 16 and 21. The end effector may thus be articulated, if desired, following firing of the staples and cutting of the tissue since the actuation shafts are no longer being pressed together. In other words, the locking mechanism is in its locked configuration during the cam's sliding along the intermediate planar surface 406i and the cam's seating the groove 400a to lock the end effector's articulated position and otherwise in its unlocked configuration to allow free articulation of the end effector. Movement of the firing rod 404 proximally from its position in FIGS. 16 and 21 back to its position in FIG. 17 pulls the movable wedge proximally and resets the locking mechanism to its unlocked configuration for any subsequent firing actuation.

Figure 22:
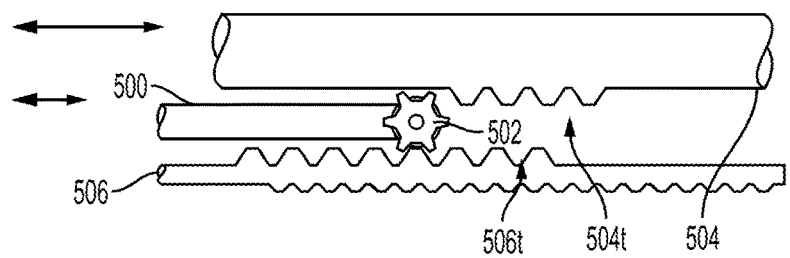
FIG. 22 is a side schematic view of a portion of another embodiment of a surgical tool.

FIG. 22 illustrates another embodiment of a surgical tool configured similar to the surgical tool of FIG. 10, e.g., includes a pair of movable actuation shafts, but including a locking mechanism configured to be automatically moved from its unlocked configuration to its locked configuration in response to actuation of the surgical tool's cutting element. In this illustrated embodiment, the locking mechanism includes a stationary wedge, a movable wedge, a locking rod 500, and a gear or pinion 502 attached to the locking rod 500. The locking rod 500 has a hook at its distal end that hooks the movable wedge, similar to the hook 206h discussed above, except that the hook in this illustrated embodiment faces distally similar to the hook 400h discussed above. The gear 502 is attached to the locking rod 500 at a proximal end thereof via a pin about which the gear 502 is configured to rotate relative to the locking rod 500, although the gear 502 may be attached to the locking rod 500 in other ways.

The surgical tool also includes a firing rod 504 that is configured to be actuated to cause the firing of staples from the surgical tool's end effector and translate a cutting element along the end effector. The firing rod 504 is generally configured and used similar to the firing bar 64 of FIGS. 5 and 6. The firing rod 504 has teeth 504t thereon that are configured to operatively engage the gear 502.

The surgical tool also includes a proximal channel retainer 506 that is configured to guide the translational movement of the firing rod 504. The proximal channel retainer 506 is generally configured and used similar to the proximal channel retainer 406 discussed above. The proximal channel retainer 506 has teeth 506t thereon that are configured to operatively engage the gear 502.

In general, the gear 502 is configured to operatively engage the firing rod 504 (e.g., the teeth 504t thereof) and the proximal channel retainer 506 (e.g., the teeth 506t thereof) during firing, e.g., during the movement of the firing rod 504, to cause the movable wedge to move relative to the stationary wedge, e.g., to slide therealong similar to the movable and stationary wedges 208, 210 discussed above, and thereby press the first and second actuation shafts together, similar to the first and second actuation shafts 200, 202 discussed above. The gear's engagement with the teeth 504t, 506t can cause the locking rod 500 to move with the firing rod 504 and thereby slide the movable wedge along the stationary wedge to press the first and second actuation shafts together to lock the end effector at its current articulated orientation.

In use, in response to actuation of the firing rod 504, e.g., via force delivered to the surgical tool via a robotic surgical system, the firing rod 504 moves distally. The distal movement of the firing rod 504 causes the gear 502 to rotate and thereby move the locking rod 500 distally. The movable wedge hooked by the locking rod 500 thus also slides distally along the stationary wedge, thereby urging the actuation shafts together to lock the end effector at its articulated position during the firing, e.g., during the firing of staples and the cutting of tissue with the cutting element. In other embodiments, the locking rod 500 can be configured to move proximally in response to distal movement of the firing rod 504 to pull the movable wedge proximally to engage the lock, similar to the locking rod 206 of FIG. 10 discussed above. A length of the firing rod 504 along which the teeth 504*t* extend can correspond to a longer of a length that the sled translates to drive the staples out of the end effector and a length that the cutting element translates along the end effector to cut tissue engaged thereby. In at least some embodiments, these lengths may be equal. The actuation shafts may thus be pressed together throughout the cutting and firing process such that the end effector's articulation angle is locked throughout the cutting and firing process.

Continued distal movement of the firing rod 504 disengages the gear 502 from the firing rod's teeth 504*t*, as shown in FIG. 22. The end effector may thus be articulated, if desired, following firing of the staples and cutting of the tissue since the actuation shafts are no longer being pressed together. In other words, the locking mechanism is in its locked configuration during the gear's engagement with the firing rod's teeth 504*t* to lock the end effector's articulated position and otherwise in its unlocked configuration to allow free articulation of the end effector. Movement of the firing rod 504 proximally from its position in FIG. 22 pulls the movable wedge proximally and resets the locking mechanism to its unlocked configuration for any subsequent firing actuation.

Figure 23:
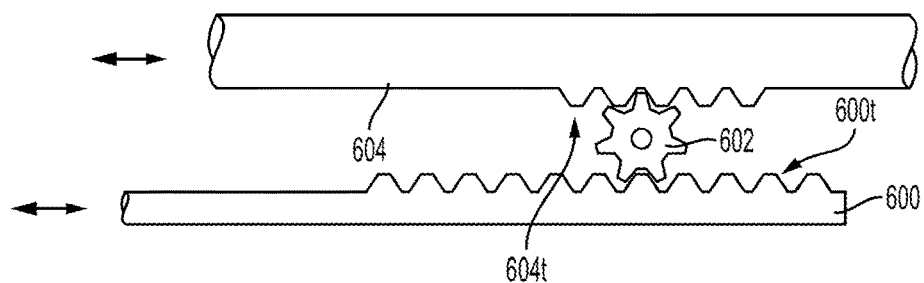
FIG. 23 is a side schematic view of a portion of yet another embodiment of a surgical tool.

FIG. 23 illustrates another embodiment of a surgical tool configured similar to the surgical tool of FIG. 10, e.g., includes a pair of movable actuation shafts, but including a locking mechanism configured to be automatically moved from its unlocked configuration to its locked configuration in response to actuation of the surgical tool's cutting element. In this illustrated embodiment, the locking mechanism includes a stationary wedge, a movable wedge, a locking rod 600, and a gear or pinion 602 configured to operatively engage teeth 600*t* of the locking rod 600. The gear 602 is secured to the surgical tool, e.g., to an inner wall of an elongate shaft thereof, with a pin, although the gear 602 can be attached to the surgical tool in other ways.

The surgical tool also includes a firing rod 604 that is configured to be actuated to cause the firing of staples from the surgical tool's end effector and translate a cutting element along the end effector. The firing rod 604 is generally configured and used similar to the firing bar 64 of FIGS. 5 and 6. The firing rod 604 has teeth 604*t* thereon that are configured to operatively engage the gear 602.

In general, the gear 602 is configured to operatively engage the firing rod 604 (e.g., the teeth 604*t* thereof) and the locking rod 600 (e.g., the teeth 600*t* thereof) during firing, e.g., during the movement of the firing rod 604, to cause the movable wedge to move relative to the stationary wedge, e.g., to slide therealong similar to the movable and stationary wedges 208, 210 discussed above, and thereby press the first and second actuation shafts together, similar to the first and second actuation shafts 200, 202 discussed above. The gear's engagement with the teeth 604*t*, 600*t* can cause the locking rod 600 to move with the firing rod 604 and thereby slide the movable wedge along the stationary wedge to press the first and second actuation shafts together to lock the end effector at its current articulated orientation.

In use, in response to actuation of the firing rod 604, e.g., via force delivered to the surgical tool via a robotic surgical system, the firing rod 604 moves distally. The distal movement of the firing rod 604 causes the gear 602 to rotate and thereby move the locking rod 600 distally. The movable wedge hooked by the locking rod 600 thus also slides distally along the stationary wedge, thereby urging the actuation shafts together to lock the end effector at its articulated position during the firing, e.g., during the firing of staples and the cutting of tissue with the cutting element. In other embodiments, the locking rod 600 can be configured to move proximally in response to distal movement of the firing rod 604 to pull the movable wedge proximally to engage the lock, similar to the locking rod 206 of FIG. 10 discussed above. A length of the firing rod 604 along which the teeth 604*t* extend can correspond to a longer of a length that the sled translates to drive the staples out of the end effector and a length that the cutting element translates along the end effector to cut tissue engaged thereby. In at least some embodiments, these lengths may be equal. The actuation shafts may thus be pressed together throughout the cutting and firing process such that the end effector's articulation angle is locked throughout the cutting and firing process.

Continued distal movement of the firing rod 604 disengages the gear 602 from the firing rod's teeth 604*t*. The end effector may thus be articulated, if desired, following firing of the staples and cutting of the tissue since the actuation shafts are no longer being pressed together. In other words, the locking mechanism is in its locked configuration during the gear's engagement with the firing rod's teeth 604*t* to lock the end effector's articulated position and otherwise in its unlocked configuration to allow free articulation of the end effector. Movement of the firing rod 604 proximally from its position in which it is not engaged with the gear 602 pulls the movable wedge proximally and resets the locking mechanism to its unlocked configuration for any subsequent firing actuation.

Figure 24:
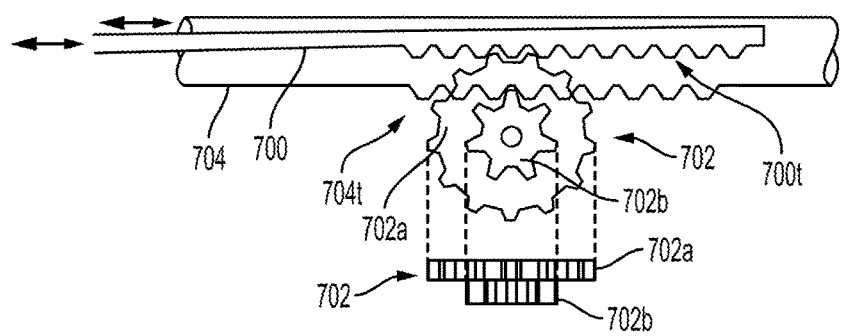
FIG. 24 is a side schematic view of a portion of still another embodiment of a surgical tool.

FIG. 24 illustrates another embodiment of a surgical tool configured similar to the surgical tool of FIG. 10, e.g., includes a pair of movable actuation shafts, but including a locking mechanism configured to be automatically moved from its unlocked configuration to its locked configuration in response to actuation of the surgical tool's cutting element. In this illustrated embodiment, the locking mechanism includes a stationary wedge, a movable wedge, a locking rod 700, and a stacked gear or pinion 702 including first and second gears or pinions 702*a*, 702*b* that are stacked on one another with a common center of rotation. The first and second gears 702*a*, 702*b* are secured to the surgical tool, e.g., to an inner wall of an elongate shaft thereof, with a pin about which the gears 702*a*, 702*b* are configured to rotate, although the gears 702*a*, 702*b* can be attached to the surgical tool in other ways. The locking rod 700 has teeth 700*t* thereon that are configured to operatively engage the first gear 702*a*.

The surgical tool also includes a firing rod 704 that is configured to be actuated to cause the firing of staples from the surgical tool's end effector and translate a cutting element along the end effector. The firing rod 704 is generally configured and used similar to the firing bar 64 of FIGS. 5 and 6. The firing rod 704 has teeth 704*t* thereon that are configured to operatively engage the second gear 702*b*. The stacked configuration of the gears 702*a*, 702*b* may allow the locking rod 700 to be stacked on the firing rod 704, as shown in FIG. 24, which may conserve space within the surgical tool's elongate shaft and thus allow the tool to be smaller and/or free space within the elongate shaft for other tool components.

In general, the stacked pinion 702 is configured to operatively engage the firing rod 704 and the locking rod 700 during firing, e.g., during the movement of the firing rod 704, to cause the movable wedge to move relative to the stationary wedge, e.g., to slide therealong similar to the movable and stationary wedges 208, 210 discussed above, and thereby press the first and second actuation shafts together, similar to the first and second actuation shafts 200, 202 discussed above. Namely, during firing, the second gear 702b is configured to operatively engage the firing rod 704 (e.g., the teeth 704t thereof) and the first gear 702a is configured to operatively engage the locking rod 700 (e.g., the teeth 700t thereof). The gears' engagement with the teeth 704t, 700t can cause the locking rod 700 to move with the firing rod 704 and thereby slide the movable wedge along the stationary wedge to press the first and second actuation shafts together to lock the end effector at its current articulated orientation.

In use, in response to actuation of the firing rod 704, e.g., via force delivered to the surgical tool via a robotic surgical system, the firing rod 704 moves distally. The distal movement of the firing rod 704 causes the second gear 702b to rotate and thereby cause rotation of the first gear 702a operatively engaged with the second gear 702b. The rotation of the first gear 702a causes the locking rod 700 to move distally. The movable wedge hooked by the locking rod 700 thus also slides distally along the stationary wedge, thereby urging the actuation shafts together to lock the end effector at its articulated position during the firing, e.g., during the firing of staples and the cutting of tissue with the cutting element. In other embodiments, the locking rod 700 can be configured to move proximally in response to distal movement of the firing rod 704 to pull the movable wedge proximally to engage the lock, similar to the locking rod 206 of FIG. 10 discussed above. A length of the firing rod 704 along which the teeth 704t extend can correspond to a longer of a length that the sled translates to drive the staples out of the end effector and a length that the cutting element translates along the end effector to cut tissue engaged thereby. In at least some embodiments, these lengths may be equal. The actuation shafts may thus be pressed together throughout the cutting and firing process such that the end effector's articulation angle is locked throughout the cutting and firing process.

Continued distal movement of the firing rod 704 disengages the second gear 702b from the firing rod's teeth 704t. The end effector may thus be articulated, if desired, following firing of the staples and cutting of the tissue since the actuation shafts are no longer being pressed together. In other words, the locking mechanism is in its locked configuration during the second gear's engagement with the firing rod's teeth 704t to lock the end effector's articulated position and otherwise in its unlocked configuration to allow free articulation of the end effector. Movement of the firing rod 704 proximally from its position in which it is not engaged with the second gear 702b pulls the movable wedge proximally and resets the locking mechanism to its unlocked configuration for any subsequent firing actuation.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 25:
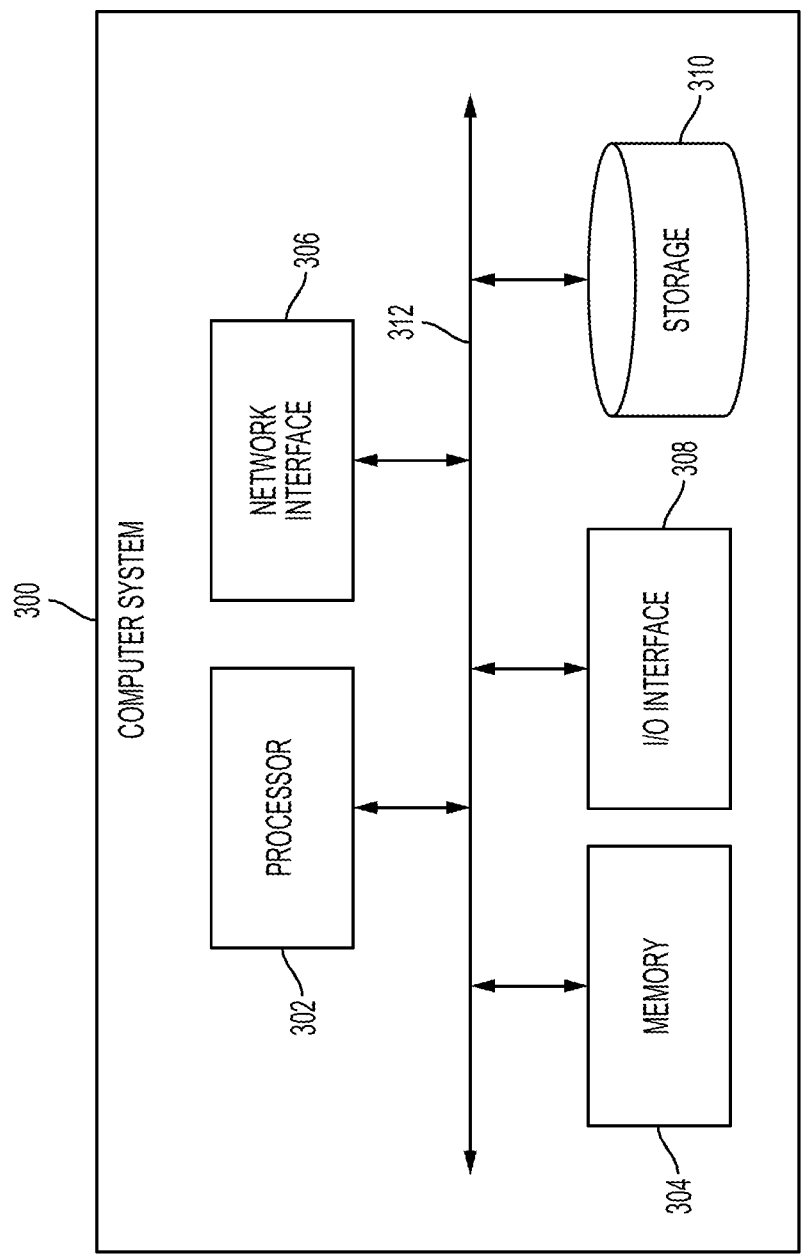
FIG. 25 is a schematic view of one embodiment of a computer system.

FIG. 25 illustrates one exemplary embodiment of a computer system 300. As shown, the computer system 300 includes one or more processors 302 which can control the operation of the computer system 300. "Processors" are also referred to herein as "controllers." The processor(s) 302 can include any type of microprocessor or central processing unit (CPU), including programmable general-purpose or special-purpose microprocessors and/or any one of a variety of proprietary or commercially available single or multi-processor systems. The computer system 300 can also include one or more memories 304, which can provide temporary storage for code to be executed by the processor(s) 302 or for data acquired from one or more users, storage devices, and/or databases. The memory 304 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 300 can be coupled to a bus system 312. The illustrated bus system 312 is an abstraction that represents any one or more separate physical busses, communication lines/interfaces, and/or multi-drop or point-to-point connections, connected by appropriate bridges, adapters, and/or controllers. The computer system 300 can also include one or more network interface(s) 306, one or more input/output (IO) interface(s) 308, and one or more storage device(s) 310.

The network interface(s) 306 can enable the computer system 300 to communicate with remote devices, e.g., other computer systems, over a network, and can be, for non-limiting example, remote desktop connection interfaces, Ethernet adapters, and/or other local area network (LAN) adapters. The IO interface(s) 308 can include one or more interface components to connect the computer system 300 with other electronic equipment. For non-limiting example, the IO interface(s) 308 can include high speed data ports, such as universal serial bus (USB) ports, 1394 ports, Wi-Fi, Bluetooth, etc. Additionally, the computer system 300 can be accessible to a human user, and thus the IO interface(s) 308 can include displays, speakers, keyboards, pointing devices, and/or various other video, audio, or alphanumeric interfaces. The storage device(s) 310 can include any conventional medium for storing data in a non-volatile and/or non-transient manner. The storage device(s) 310 can thus hold data and/or instructions in a persistent state, i.e., the value(s) are retained despite interruption of power to the computer system 300. The storage device(s) 310 can include one or more hard disk drives, flash drives, USB drives, optical drives, various media cards, diskettes, compact discs, and/or any combination thereof and can be directly connected to the computer system 300 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 25 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 300 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 300 can also include a web server for generating and/or delivering the web pages to client computer systems.

In an exemplary embodiment, the computer system 300 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   an elongate shaft;
   an end effector at a distal end of the elongate shaft, the end effector being configured to articulate at an angle relative to a longitudinal axis of the elongate shaft;
   a cutting element configured to move longitudinally along the end effector to cut tissue engaged by the end effector; and
   a locking mechanism configured to lock the end effector at the angle, wherein the movement of the cutting element along the end effector is configured to cause the locking mechanism to lock the end effector at the angle.

2. The device of claim 1, further comprising first and second rods configured to move longitudinally relative to the end effector to thereby cause the end effector to articulate, each of the first and second rods being configured to be operatively engaged by the locking mechanism to lock the end effector.

3. The device of claim 1, wherein the locking mechanism is configured to lock the end effector at any angle in the end effector's range of articulation.

4. The device of claim 1, further comprising a pair of plates configured to frictionally engage with one another to lock the end effector at the angle until a force is applied thereto to overcome the frictional engagement.

5. The device of claim 1, wherein the locking mechanism includes a gear having teeth configured to operatively engage corresponding teeth of a rod configured to move the cutting element, and the gear being configured to rotate during the movement of the cutting element along the end effector.

6. The device of claim 1, wherein the locking mechanism includes a plate configured to operatively engage a rod configured to move the cutting element, and the plate being configured to move longitudinally with the cutting element during the movement of the cutting element along the end effector.

7. The device of claim 1, wherein the movement of the cutting element is configured to be controlled by a robotic surgical system.

8. A surgical device, comprising:
an elongate shaft;
an end effector at a distal end of the elongate shaft, the end effector being configured to articulate at an angle relative to a longitudinal axis of the elongate shaft;
a rod configured to move longitudinally relative to the end effector to thereby cause the end effector to articulate;
a cutting element configured to move longitudinally along the end effector to cut tissue engaged by the end effector; and
a locking mechanism configured to automatically move relative to the end effector, wherein the movement of the cutting element is configured to cause the automatic movement of the locking mechanism to thereby hold the end effector at the angle.

9. The device of claim 8, wherein the locking mechanism is configured to move during the articulation of the end effector.

10. The device of claim 8, wherein the locking mechanism is configured to move during the movement of the cutting element.

11. The device of claim 8, wherein the movement of the locking mechanism includes longitudinal movement.

12. The device of claim 8, wherein the movement of the locking mechanism includes rotational movement.

13. The device of claim 8, further comprising an actuator configured to be actuated to cause the movement of the cutting element, the locking mechanism being configured to move relative to the end effector in response to the actuation of the actuator.

14. The device of claim 8, further comprising an actuator configured to be actuated to cause the articulation of the end effector, the locking mechanism being configured to move relative to the end effector in response to the actuation of the actuator.

15. The device of claim 8, wherein the locking mechanism includes a pair of surfaces configured to frictionally engage to hold the end effector at the angle until a force is applied thereto to overcome the frictional engagement.

16. The device of claim 8, wherein the locking mechanism includes a gear having teeth configured to operatively engage corresponding teeth of the rod and to rotate during the movement of the cutting element along the end effector.

17. The device of claim 8, wherein the locking mechanism includes a plate configured to operatively engage the rod and to move longitudinally with the cutting element during the movement of the cutting element along the end effector.

18. A surgical method, comprising:
actuating a first actuator of a surgical tool having an elongate shaft with an end effector at a distal end thereof, actuation of the first actuator causing the end effector to articulate at any angle up to a maximum angle relative to the elongate shaft; and
actuating a second actuator of the surgical tool to cause a cutting element of the surgical tool to move along the end effector to cut tissue engaged by the end effector;
wherein one of actuating the first actuator and actuating the second actuator causes the end effector to be locked at the angle throughout the movement of the cutting element.

19. The method of claim 18, wherein actuating the first actuator causes the end effector to be locked at the angle throughout the movement of the cutting element, and the surgical tool includes a pair of plates configured to engage at a first coefficient of friction in response to the actuation of the first actuator.

20. The method of claim 18, wherein actuating the second actuator causes the end effector to be locked at the angle throughout the movement of the cutting element, actuating the first actuator causes longitudinal movement of an articulation rod to effect the articulation of the end effector, and the surgical tool includes a movable locking mechanism that moves into engagement with the articulation rod to lock the end effector at the angle throughout the movement of the cutting element.

* * * * *